US012761088B2

(12) United States Patent
Gao et al.

(10) Patent No.: US 12,761,088 B2
(45) Date of Patent: Oct. 13, 2026

(54) FORCE SENSING DEVICE FOR MONITORING INSERTION FORCE OF A MEDICAL DEVICE

(71) Applicant: THE REGENTS OF THE UNIVERSITY OF CALIFORNIA, Oakland, CA (US)

(72) Inventors: Bruce M. Gao, Orange, CA (US); Ralph V. Clayman, Orange, CA (US); Benjamin Dolan, Irvine, CA (US); Andrei Cumpanas, Orange, CA (US); Aymon N. Ali, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 19/084,420

(22) Filed: Mar. 19, 2025

(65) Prior Publication Data

US 2025/0216274 A1 Jul. 3, 2025

Related U.S. Application Data

(63) Continuation-in-part of application No. 17/570,776, filed on Jan. 7, 2022, now abandoned, which is a (Continued)

(51) Int. Cl.

| | |
|---|---|
| ***G01L 1/02*** | (2006.01) |
| ***A61M 25/00*** | (2006.01) |
| ***G01L 5/00*** | (2006.01) |

(52) U.S. Cl.

CPC ............. *G01L 1/02* (2013.01); *A61M 25/003* (2013.01); *G01L 5/0038* (2013.01)

(58) Field of Classification Search

CPC ....... G01L 7/18–24; G01L 7/185; G01L 7/16; A61M 2025/0002; A61B 2017/2425–3429; A61B 17/3423

(Continued)

(56) References Cited

U.S. PATENT DOCUMENTS 4,476,866 A * 10/1984 Chin ............... A61M 25/10182 604/920
4,632,669 A * 12/1986 Phipps, Sr. ..... A61M 25/10182 604/920

(Continued)

FOREIGN PATENT DOCUMENTS

WO 2004/087262 A2 10/2004

OTHER PUBLICATIONS

WIPO, "International Search Report and Written Opinion" issued in connection with PCT Patent Application PCT/US2025/020571, dated May 15, 2025, 15 pages.

(Continued)

*Primary Examiner* — Tran M. Tran

(74) *Attorney, Agent, or Firm* — NGUYEN TARBET IP LAW

(57) ABSTRACT

A force sensing device and monitoring system for use in medical procedures, featuring an air-based sensor to quantify force applied during insertion of a ureteral access sheath (UAS), catheter, or other medical instrument. The invention features a pneumatic syringe mechanism, wherein force is measured by compressing an occluded syringe, translating pressure changes into a measurable force output. Real-time feedback is provided via visual, tactile, or auditory indicators, signaling predefined force thresholds (e.g., 4 N, 6 N, and 8 N) to prevent excessive pressure and resultant tissue injury. The invention provides precise, cost-effective, and widely accessible force monitoring without reliance on (Continued)

electronics or Bluetooth® systems, in various surgical fields, including laparoscopy, robotic-assisted surgery, endoscopic procedures, and vascular catheterization, ensuring safe instrument deployment and minimizing complications. The sensor can be integrated into existing medical instruments via Luer-Lock or similar interface connections and may be disposable or reusable.

17 Claims, 29 Drawing Sheets

Related U.S. Application Data continuation-in-part of application No. 15/963,851, filed on Apr. 26, 2018, now abandoned.

(60) Provisional application No. 63/567,254, filed on Mar. 19, 2024, provisional application No. 62/491,011, filed on Apr. 27, 2017.

(58) Field of Classification Search
USPC .................................................. 604/264–288
See application file for complete search history.

(56) References Cited

U.S. PATENT DOCUMENTS 4,820,283 A 4/1989 Schickling et al.
5,431,645 A 7/1995 Smith et al.
5,533,969 A * 7/1996 Mulder ........... A61M 25/10187 604/100.02
6,164,139 A * 12/2000 Krimmer ................ G01L 19/10 73/146.8
6,375,471 B1 4/2002 Wendlandt et al.
6,981,945 B1 1/2006 Sarvazyan et al.
7,316,677 B1 1/2008 Dulak et al.
7,437,943 B2 10/2008 Munz et al.
7,931,588 B2 4/2011 Sarvazyan et al.
8,202,251 B2 6/2012 Bierman et al.
8,282,622 B2 * 10/2012 Dulak ............... A61M 25/0662 604/164.01
8,388,518 B2 3/2013 Sarvazyan et al.
8,840,628 B2 9/2014 Green et al.
9,078,682 B2 7/2015 Lenker et al.
9,155,859 B2 * 10/2015 Dulak ............... A61M 25/0017
9,192,406 B2 11/2015 Doud et al.
9,211,160 B2 12/2015 Pivotto et al.
9,220,834 B2 * 12/2015 Vilks ................. A61M 25/0009
9,358,072 B2 * 6/2016 Ullrich ................... A61B 34/70
9,585,660 B2 3/2017 Laurent et al.
9,603,667 B2 3/2017 Yang et al.
9,668,719 B2 * 6/2017 Tegels .................... A61B 34/76
9,677,961 B2 * 6/2017 Chou ...................... F16K 37/00
9,788,910 B2 10/2017 Schuh
9,839,393 B2 12/2017 Verma
10,004,521 B2 6/2018 Shelton et al.
10,013,082 B2 7/2018 Schecter
10,143,489 B2 12/2018 Kobayashi et al.
10,179,046 B2 1/2019 Levi
10,182,705 B2 1/2019 Ramsey
10,454,347 B2 10/2019 Covington et al.
10,565,899 B1 2/2020 Dignam et al.
10,631,945 B2 4/2020 Eschbach et al.
11,027,099 B2 * 6/2021 Bierman ........... A61M 25/0606
11,185,245 B2 * 11/2021 McKinney ........... A61B 5/4519
11,285,301 B2 * 3/2022 Ornelas Vargas .. A61M 25/065
11,389,264 B2 * 7/2022 Clayman ............... A61M 25/01
11,402,287 B2 * 8/2022 Alkhrdaji .............. G01L 19/141
11,609,138 B2 * 3/2023 Chou ...................... G01L 19/16
11,628,279 B2 * 4/2023 Chu ................... A61B 17/3421 604/528
11,650,118 B2 * 5/2023 Moruzzi ................. G01L 19/08 73/861.42
11,712,543 B2 * 8/2023 Bierman ........... A61M 25/0606 604/510
11,918,357 B2 * 3/2024 Devgon ........... A61B 5/150732
12,163,866 B2 * 12/2024 Hund .................. G01M 3/3209
12,239,814 B2 * 3/2025 Solomon ............ A61M 39/1011
2004/0068203 A1 * 4/2004 Gellman .................. A61B 5/22 600/587
2006/0217687 A1 9/2006 Bakos et al.
2006/0231013 A1 * 10/2006 Lane ....................... G01L 7/166 116/272
2009/0306472 A1 12/2009 Filipi et al.
2012/0172891 A1 7/2012 Lee
2014/0025036 A1 1/2014 Bierman et al.
2016/0183819 A1 * 6/2016 Burnett ................ A61B 5/0084 600/561
2016/0367368 A1 12/2016 Vidlund et al.
2017/0224370 A1 8/2017 Loreth
2018/0177516 A1 6/2018 Vardi et al.
2018/0199799 A1 7/2018 Chu
2018/0311468 A1 * 11/2018 Clayman ........... A61M 25/0668
2019/0076209 A1 3/2019 Clayman et al.
2019/0083753 A1 3/2019 Chu
2022/0126066 A1 4/2022 Clayman et al.

OTHER PUBLICATIONS

USPTO, "Non-Final Office Action", issued in connection with U.S. Appl. No. 17/570,776, dated Mar. 10, 2025, 17 pages.
Koo et al., "The Impact of Preoperative α-Adrenergic Antagonists on Ureteral Access Sheath Insertion force and the Upper Limit of Force Required to Avoid Ureteral Mucosal Injury: A Randomized Controlled Study", The Journal of Urology, https://doi.org/10.1016/j.juro.2017.09.173, vol. 199, Jun. 2018, pp. 1622-1630.
Tapiero et al. "Assessing Threshold for Injury", The Journal of Urology, vol. 201, No. 4S, May 3, 2019, 2 pages.

* cited by examiner

- Volume at 4N (cc) – 0.295 +/-0.010
- Volume at 6N (cc) – 0.198 +/- 0.006
- Volume at 8N (cc) – 0.145 +/- 0.006

- The measurements were consistent across different prototypes of the same syringe and all 3 force sensor thresholds (4 N, 6 N, 8 N, respectively).

FIG.8

| Lot Number | Brand | Initial Volume (mL) | Volume at 4N (mL) | | | | | Volume at 6N (mL) | | | | | Volume at 8N (mL) | | | | |
|---|---|---|---|---|---|---|---|---|---|---|---|---|---|---|---|---|---|
| | | | 1 | 2 | 3 | 4 | 5 | 1 | 2 | 3 | 4 | 5 | 1 | 2 | 3 | 4 | 5 |
| 3207362-8 | BD - Glass | 1 | 0.31 | 0.3 | 0.28 | 0.28 | 0.28 | 0.2 | 0.2 | 0.19 | 0.2 | 0.2 | 0.14 | 0.15 | 0.14 | 0.14 | 0.14 |
| 3207362-9 | BD - Glass | 1 | 0.3 | 0.29 | 0.29 | 0.27 | 0.29 | 0.21 | 0.2 | 0.2 | 0.19 | 0.2 | 0.15 | 0.14 | 0.14 | 0.14 | 0.15 |
| 3207362-14 | BD - Glass | 1 | 0.31 | 0.3 | 0.3 | 0.3 | 0.3 | 0.2 | 0.21 | 0.2 | 0.2 | 0.2 | 0.16 | 0.15 | 0.15 | 0.14 | 0.15 |
| 3207362-15 | BD - Glass | 1 | 0.3 | 0.29 | 0.3 | 0.3 | 0.3 | 0.2 | 0.2 | 0.2 | 0.2 | 0.19 | 0.14 | 0.15 | 0.14 | 0.15 | 0.15 |
| 3212115-16 | BD- Glass | 1 | 0.3 | 0.29 | 0.3 | 0.29 | 0.3 | 0.2 | 0.2 | 0.19 | 0.18 | 0.2 | 0.14 | 0.14 | 0.15 | 0.14 | 0.15 |
| 2336605-1 | BD tuberculin | 1 | 0.33 | 0.31 | 0.31 | 0.31 | 0.29 | 0.22 | 0.21 | 0.2 | 0.2 | 0.2 | 0.16 | 0.15 | 0.15 | 0.15 | 0.14 |
| 2336605-2 | BD tuberculin | 1 | 0.31 | 0.32 | 0.34 | 0.34 | 0.36 | 0.22 | 0.22 | 0.22 | 0.22 | 0.22 | 0.15 | 0.15 | 0.15 | 0.15 | 0.14 |
| 2336605-3 | BD tuberculin | 1 | 0.32 | 0.32 | 0.34 | 0.34 | 0.34 | 0.22 | 0.21 | 0.22 | 0.21 | 0.21 | 0.1 | 0.15 | 0.15 | 0.14 | 0.15 |
| 3018950-4 | BD tuberculin | 1 | 0.35 | 0.35 | 0.36 | 0.37 | 0.35 | 0.24 | 0.22 | 0.24 | 0.25 | 0.24 | 0.15 | 0.16 | 0.17 | 0.17 | 0.17 |
| 3018950-5 | BD tuberculin | 1 | 0.33 | 0.34 | 0.33 | 0.32 | 0.33 | 0.22 | 0.22 | 0.22 | 0.22 | 0.21 | 0.16 | 0.16 | 0.16 | 0.16 | 0.16 |
| 210402-1 | Berpu | 1 | 0.31 | 0.3 | 0.3 | 0.3 | 0.3 | 0.21 | 0.22 | 0.21 | 0.21 | 0.2 | 0.16 | 0.16 | 0.17 | 0.16 | 0.16 |
| 210402-2 | Berpu | 1 | 0.3 | 0.3 | 0.3 | 0.3 | 0.3 | 0.21 | 0.21 | 0.21 | 0.21 | 0.2 | 0.16 | 0.17 | 0.16 | 0.16 | 0.16 |
| 210402-3 | Berpu | 1 | 0.32 | 0.31 | 0.3 | 0.31 | 0.31 | 0.21 | 0.21 | 0.21 | 0.22 | 0.22 | 0.16 | 0.16 | 0.16 | 0.16 | 0.16 |
| 210402-4 | Berpu | 1 | 0.3 | 0.3 | 0.3 | 0.3 | 0.3 | 0.21 | 0.21 | 0.21 | 0.21 | 0.2 | 0.16 | 0.17 | 0.16 | 0.16 | 0.16 |
| 210402-5 | Berpu | 1 | 0.32 | 0.32 | 0.33 | 0.32 | 0.32 | 0.23 | 0.23 | 0.23 | 0.23 | 0.23 | 0.17 | 0.17 | 0.17 | 0.18 | 0.17 |

| | 4N Volume (cc) | SD (cc) | 6N Volume (cc) | SD (cc) | 8N Volume (cc) | SD (cc) |
|---|---|---|---|---|---|---|
| **BD-Glass** | 0.295 | 0.010 | 0.198 | 0.006 | 0.145 | 0.006 |
| **BD Tuberculin** | 0.332 | 0.019 | 0.219 | 0.013 | 0.152 | 0.014 |
| **Berpu** | 0.307 | 0.009 | 0.214 | 0.010 | 0.164 | 0.006 |

| | vs. | **Luer Lok™** | **Tuberculin** | **Luer Slip** |
|---|---|---|---|---|
| **4 Newtons** | **Luer Lok™** | | 0.010 vs 0.019 (*p*=0.026) | 0.010 vs. 0.009 (*p*=0.609) |
| | **Tuberculin** | 0.019 vs. 0.010 (*p*=0.026) | | 0.019 vs. 0.009 (*p*=0.0005) |
| | **Luer Slip** | 0.009 vs. 0.010 (*p*=0.609) | 0.009 vs. 0.019 (*p*=0.0005) | |
| **6 Newtons** | **Luer Lok™** | | 0.006 vs. 0.013 (*p*=0.0003) | 0.006 vs. 0.010 (*p*=0.015) |
| | **Tuberculin** | 0.013 vs. 0.006 (*p*=0.0003) | | 0.013 vs. 0.010 (*p*=0.206) |
| | **Luer Slip** | 0.010 vs. 0.006 (*p*=0.015) | 0.010 vs. 0.013 (*p*=0.206) | |
| **8 Newtons** | **Luer Lok™** | | 0.006 vs. 0.014 (*p*<0.0001) | 0.006 vs. 0.006 (*p*=1) |
| | **Tuberculin** | 0.014 vs. 0.006 (*p*<0.0001) | | 0.014 vs. 0.006 (*p*<0.0001) |
| | **Luer Slip** | 0.006 vs. 0.006 (*p*=1) | 0.006 vs. 0.014 (*p*<0.0001) | |

FIG. 63

FORCE SENSING DEVICE FOR MONITORING INSERTION FORCE OF A MEDICAL DEVICE

CROSS-REFERENCE TO RELATED APPLICATIONS

This application is a non-provisional and claims benefit of U.S. Provisional Application No. 63/567,254 filed Mar. 19, 2024, the specification of which is incorporated herein in their entirety by reference.

This application is a continuation-in-part and claims benefit of U.S. patent application Ser. No. 17/570,776 filed Jan. 7, 2022, which is a continuation-in-part and claims benefit of U.S. patent application Ser. No. 15/963,851 filed Apr. 26, 2018, which is a non-provisional application and claims benefit of U.S. Provisional Application No. 62/491,011 filed Apr. 27, 2017, the specifications of which are incorporated herein in their entirety by reference.

FIELD OF THE INVENTION

The present disclosure relates to the field of medical devices, specifically procedural or surgical devices, in particular, to a sensor and monitoring device.

BACKGROUND OF THE INVENTION

Retrograde intrarenal surgery (RIRS) is the gold standard for the management and treatment of kidney stones less than 2 centimeters. In RIRS, sheaths and endoscopic instruments are passed up the ureter to allow for minimally invasive and incisionless access to the kidney. Ureteral access sheaths (UAS) facilitate stone treatment by allowing for the repeated and safe passage of the flexible ureteroscope into the kidney while decreasing intrarenal pressure, postoperative infection, and operative time. Despite these benefits, there exists a concern about UAS-induced ureteral injury, with previous studies reporting low-grade injuries in 47.8% of patients and high-grade injuries—involving splitting of the urothelium to the adipose layer—in 23.8% of patients.

It has been postulated that the mechanism of ureteral injury during UAS deployment is related to the surgical force required to deploy the UAS up the ureter. Porcine studies utilizing a proprietary University of California, Irvine force sensor (UCI-FS) (FIG. 1) characterized the forces exerted upon the ureteral wall during UAS insertion—demonstrating that high-grade ureteral injuries were noted at a force greater than 8 Newtons (N).

A subsequent prospective UCI-FS randomized clinical trial involving 210 anatomically normal renal units (no reconstruction, radiation, transplantation, or non-conventional anatomy) demonstrated that a surgical force less than 8 N during UAS deployment averted high-grade ureteral injury. In this study, an insertion force of ≤6 N was recommended for the safe passage of UAS and allowed for a 16 Fr UAS to be safely deployed in 127 (61%) patients. These findings underscore the importance of continuous and precise force monitoring during UAS insertion to mitigate the risk of high-grade ureteral injury while optimizing the size of the UAS deployed.

Despite the importance of surgical force monitoring during UAS insertion, the UCI-FS is not currently widely available. The UCI-FS is a complex, Bluetooth® reliant, electrically powered instrument that detects an applied force through a lever connected to an internal spring. Although capable of measuring forces in the 100ths of a Newton, there is currently no convenient way for all urologists to acquire one. Given these limitations, the present invention features a new, easily assembled, accessible, and affordable force sensor called "air-force one" that any urologist worldwide could use.

The "air-force one" principle revolves around the application of Boyle's Law ($P_1V_1=P_2V_2$). In an air-tight and occluded 1 mL syringe, compression of the syringe to a specific volume requires a specific amount of pressure. In this system, the initial pressure $P_1$ is known (atmospheric pressure), the initial volume $V_1$ is known (1 mL), and the final volume $V_2$ is known (the final volume to which the air is compressed). Accordingly, the final pressure $P_2$ can be calculated. This value can be converted to force given that pressure equals force divided by area ($P=F/A$). The area is the area of the inner circular diameter of the 1 ml syringe.

Given that 6 N and 8 N are thresholds of crucial importance during RIRS and UAS insertion, the above principle may be used to estimate the amount to compress an occluded 1 mL syringe to indicate these force thresholds. Therefore, benchtop testing was conducted with the validated UCI-FS and various 1 mL syringes at a hospital to determine the volume threshold corresponding to 4 N, 6 N, and 8 N of surgical force.

BRIEF SUMMARY OF THE INVENTION

It is an objective of the present invention to provide systems, devices, and methods that allow for the measurement of force applied to an insertion sheath or other medical devices, instruments, needles, retractors, catheters, or the like, during medical procedures providing indication to the user about safe force and thresholds for dangerous forces, as specified in the independent claims. Embodiments of the invention are given in the dependent claims.

Embodiments of the present invention can be freely combined with each other if they are not mutually exclusive.

In some aspects, the invention disclosed is a simplified force measurement device for catheter and sheath insertion procedures that alerts the user (e.g., a urologist) to critical levels of force during the passage of the ureteral access sheath (e.g., at 4, 6, and 8 Newtons or just at 6 N). Currently, the device of the present invention has been tested and directed towards force measurement during urologic procedures for urolithiasis in which a ureteral access sheath is inserted; however, the device may be utilized on a broader level when passing any catheter, needle, or other devices into the human body or when retracting tissues that may be delicate (e.g., veins or nerves) once the force threshold of each of these tissues is defined.

The present invention features an "air-based force sensor," which is an air-tight and enclosed pneumatic syringe system filled with room air that can be attached to any surgical device via a distal luer lock connector to monitor surgical force (i.e., to facilitate safe insertion of a surgical instrument up the ureter when passed over a preplaced guidewire). While designed to monitor surgical force during instrument insertion up the ureter, other possible applications may include situations in which a guidewire is not preplaced such as Veress needle entry into the peritoneal cavity, laparoscopic trocar placement, percutaneous renal access or deployment of surgical retractors (as to not tear the retracted tissue), foley catheter insertion, use of robot assisted instruments, as well as the passage of a variety of endoscopes be they rigid or flexible into any bodily orifice.

One of the unique and inventive technical features of the present invention is the novel air-based force sensor. Without wishing to limit the invention to any theory or mechanism, it is believed that this technical feature advantageously provides for an accurate threshold-based force sensor that, in some embodiments, can be assembled easily with materials readily available in any operating room, thereby allowing surgeons globally to create their own force sensor to safely deploy instruments. This use of an occluded syringe is unique, as it involves no injection but instead requires obstruction of the outlet, so the air within the syringe is compressed as force is applied to the plunger when the plunger is initially positioned at the highest volume mark. Moreover, the current unique injectionless dual barrel syringe with a central channel through which a guidewire may pass or single barrel syringe with a central hollow cylinder over which the plunger of the syringe passes without any encumbrance of the guidewire which passes through the central hollow cylinder or single barrel syringe with an adjacent guidewire channel. None of the presently known prior references or works have the unique inventive technical feature of the present invention.

Moreover, the prior references teach away from the present invention. For example, the prior art teaches of Bluetooth® reliant, electrically powered instruments that detect an applied force through a lever connected to an internal spring. This highly sophisticated force sensor was capable of measuring forces in the 100ths of a Newton. However, the present invention is a far simpler force sensor that utilizes a pneumatic rather than mechanical system to detect force. Furthermore, the present invention is more accessible and budget-friendly and is not prone to electronic or Bluetooth® connection-based complexities.

Furthermore, the inventive technical features of the present invention contributed to a surprising result. For example, the 4 N, 6 N, and 8 N thresholds were reliably reproduced over multiple benchtop trials with a variety of 1 cc syringes. Moreover, this approach has now been applied clinically and has precluded ureteral injury in more than 20 consecutive cases.

According to some embodiments, the present invention features a force sensing device. The device may comprise a tube comprising a first end, a second end, a first lumen, and a second lumen disposed within the first lumen, wherein the first end comprises an opening and the second end is occluded, wherein the first lumen is airtight; a plunger slidably coupled to the second lumen, wherein the plunger comprises a first plunger end and a second plunger end having a handle disposed thereon, wherein the first plunger end is disposed through the opening of the tube and within the first lumen, wherein the plunger comprises a plunger lumen through the first plunger end to the second plunger end, wherein the plunger lumen and the second lumen of the tube are fluidly coupled; and an outer casing disposed over at least a portion of the tube and at least a portion of the plunge. The outer casing comprises a first casing end, a second casing end, and a lumen, wherein the first casing end comprises a first opening and the second casing end comprises a second opening for accessing the lumen. When the handle of the plunger is pushed towards the first end of the tube, the plunger compresses a fluid within the first lumen of the tube, wherein the compression of the fluid corresponds to an applied force.

In some embodiments, the second lumen is centrally disposed within the first lumen of the tube. In some embodiments, the outer casing is cylindrical. In some embodiments, the second end of the tube further comprises an interface for a medical device. The medical device may be a ureteral access sheath (UAS), an endoscope, a ureteroscope, a Foley catheter, an intravenous line, laparoscopic/robot trocar, or combinations thereof. In other embodiments, the medical device is a laparoscopic surgical device, a laparoscopic trocar, a robotic surgical device, a minimally invasive surgical device, a Veress needle, a percutaneous renal access device, a surgical retractor, or combinations thereof.

In some embodiments, the interface comprises a Luer-Lock style interface. In other embodiments, the interface comprises a pressure fitting interface, a Luer Slip style interface, a Tuberculin-style interface, or a twist-to-connect coupling interface. In some embodiments, the interface is positioned distal to ureteral access sheath (UAS) point of insertion. In some embodiments, the device is a pneumatic device and the fluid is air. In other embodiments, the device is a hydraulic device and the fluid is a liquid.

In some embodiments, the device may further comprise a visual indicator. The visual indicator indicates an applied force of 4 Newtons, 6 Newtons, 8 Newtons, or other desired force threshold(s), or combinations thereof. In other embodiments, the device may further comprise at least one of a tactile indicator or an auditory indicator. The at least one tactile indicator or auditory indicator indicates, an applied force of 4 Newtons, 6 Newtons, or 8 Newtons, or other desired force threshold(s), or combinations thereof.

According to some embodiments, the present invention provides a method of monitoring insertion force of a medical device. The method may comprise attaching a force sensing device of the present invention to a medical device, and inserting the medical device into a patient. In some embodiments, the force sensing device may comprise a tube comprising a first end, a second end, a first lumen, and a second lumen disposed within the first lumen, wherein the first end comprises an opening and the second end is occluded, wherein the first lumen is essentially airtight; a plunger slidably coupled to the second lumen, wherein the plunger comprises a first plunger end and a second plunger end having a handle disposed thereon, wherein the first plunger end is disposed through the opening of the tube and within the first lumen, wherein the plunger comprises a plunger lumen through the first plunger end to the second plunger end, wherein the plunger lumen and the second lumen of the tube are fluidly coupled; and an outer casing disposed over at least a portion of the tube and at least a portion of the plunger, wherein the outer casing comprises a first casing end, a second casing end, and a lumen, wherein the first casing end comprises a first opening and the second casing end comprises a second opening for accessing the lumen. When the handle of the plunger is pushed towards the first end of the tube during the insertion of the medical device into the patient, the plunger compresses a fluid within the first lumen of the tube, wherein the compression of the fluid corresponds to an applied force.

In some embodiments, the device is attached to a distal end of the medical device. In some embodiments, the medical device is a ureteral access sheath (UAS), an endoscope, a ureteroscope, a Foley catheter, an intravenous line, or combinations thereof. In other embodiments, the medical device is a laparoscopic surgical device, a laparoscopic trocar, a robotic surgical device, a minimally invasive surgical device, a Veress needle, a percutaneous renal access device, a surgical retractor, or combinations thereof. In one embodiment, the device is a pneumatic device and the fluid is air. In another embodiment, the device is a hydraulic device and the fluid is a liquid.

In other embodiments, the present invention provides a force sensing device comprising a tube comprising a first end, a second end, a first lumen, and a second lumen disposed within the first lumen, wherein the first end comprises an opening and the second end is occluded, wherein the first lumen is airtight; a plunger slidably coupled to the second lumen, wherein the plunger comprises a first plunger end and a second plunger end having a handle disposed thereon, wherein the first plunger end is disposed through the opening of the tube and within the first lumen; and an outer casing disposed over at least a portion of the tube and at least a portion of the plunger, wherein the outer casing comprises a first casing end, a second casing end, and a lumen, wherein the first casing end comprises a first opening and the second casing end comprises a second opening for accessing the lumen. Wherein when the handle of the plunger is pushed towards the first end of the tube, the plunger compresses a fluid within the first lumen of the tube, where the compression of the fluid corresponds to an applied force. In some embodiments, the present invention provides a method of monitoring insertion force of a medical device. The method may comprise attaching the force sensing device of the present invention to a medical device, and inserting the medical device into a patient.

In some other embodiments, the present invention provides a force sensing device comprising a tube comprising a first end, a second end, a first lumen, and a second lumen disposed within the first lumen, wherein the first end comprises an opening and the second end is occluded, wherein the first lumen is airtight; a plunger slidably coupled to the second lumen, wherein the plunger comprises a first plunger end and a second plunger end having a handle disposed thereon, wherein the first plunger end is disposed through the opening of the tube and within the first lumen. When the handle of the plunger is pushed towards the first end of the tube, the plunger compresses a fluid within the first lumen of the tube, where the compression of the fluid corresponds to an applied force. In some embodiments, the present invention provides a method of monitoring insertion force of a medical device. The method may comprise attaching the force sensing device of the present invention to a medical device, and inserting the medical device into a patient.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

FIGS. 6A, 6B, 6C, 6D, 6E, and 6F show non-limiting embodiments and views of the force-sensing device described herein.

Figure 7A:
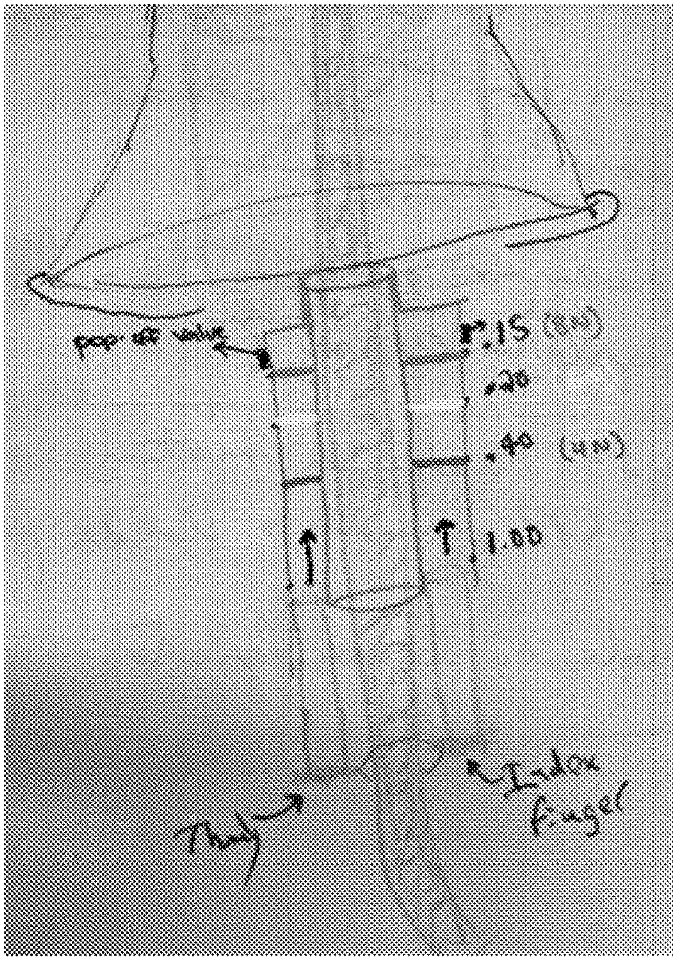
Figure 7B:
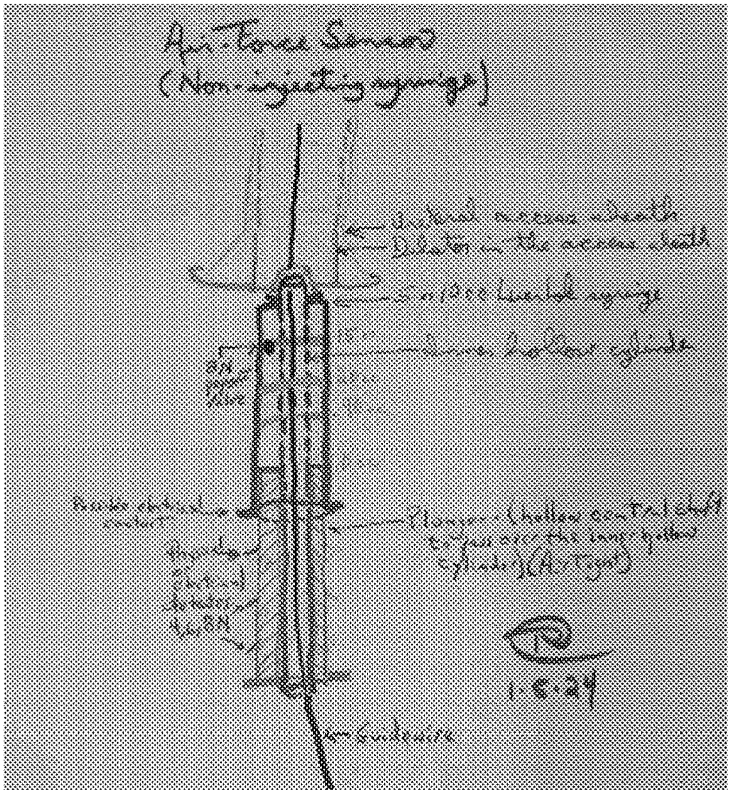

FIGS. 7A and 7B show a schematic drawing of version two (FIG. 7A) of the air force sensor—the "dual-occluder" system and (FIG. 7B) the single syringe version (5 or 10 cc barrel).

FIG. 8 shows data collected by the force sensors described herein.

Figure 9:
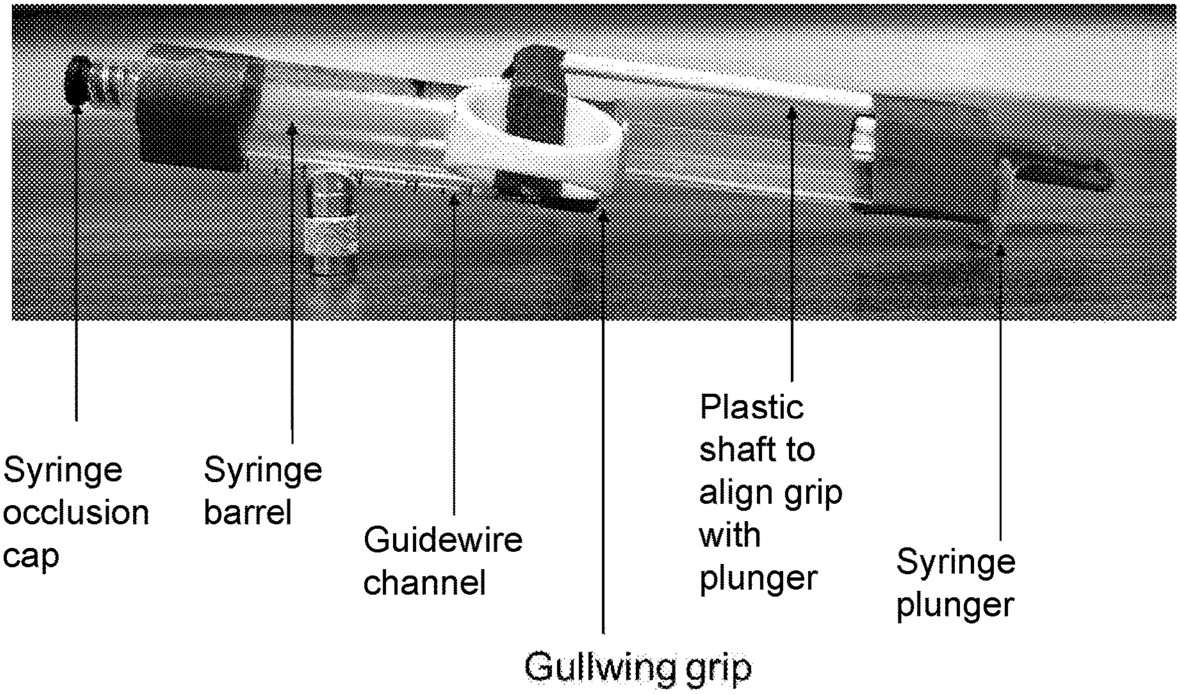

FIG. 9 shows a side view of an alternative embodiment of the force sensor wherein the first lumen and the second lumen are adjacent to each other.

Figure 10:
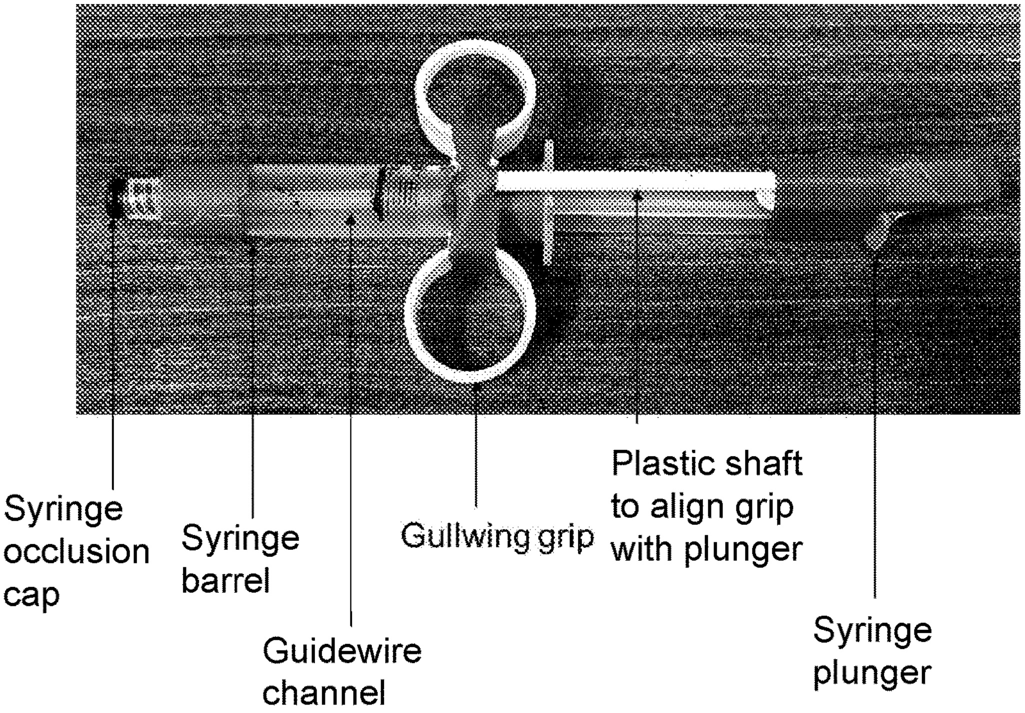

FIG. 10 shows a top view of said force sensor wherein the first lumen and the second lumen are adjacent to each other.

Figure 11:
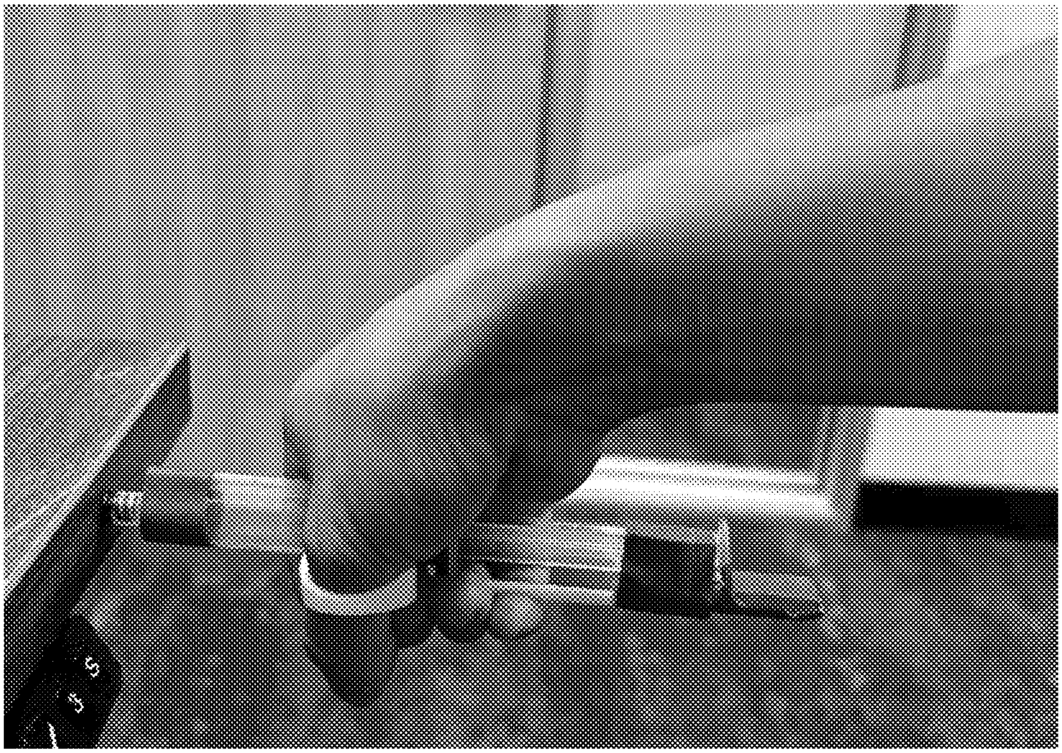

FIG. 11 shows a side view of said force sensor in simulated use, wherein the first lumen and the second lumen are adjacent to each other.

Figure 12:
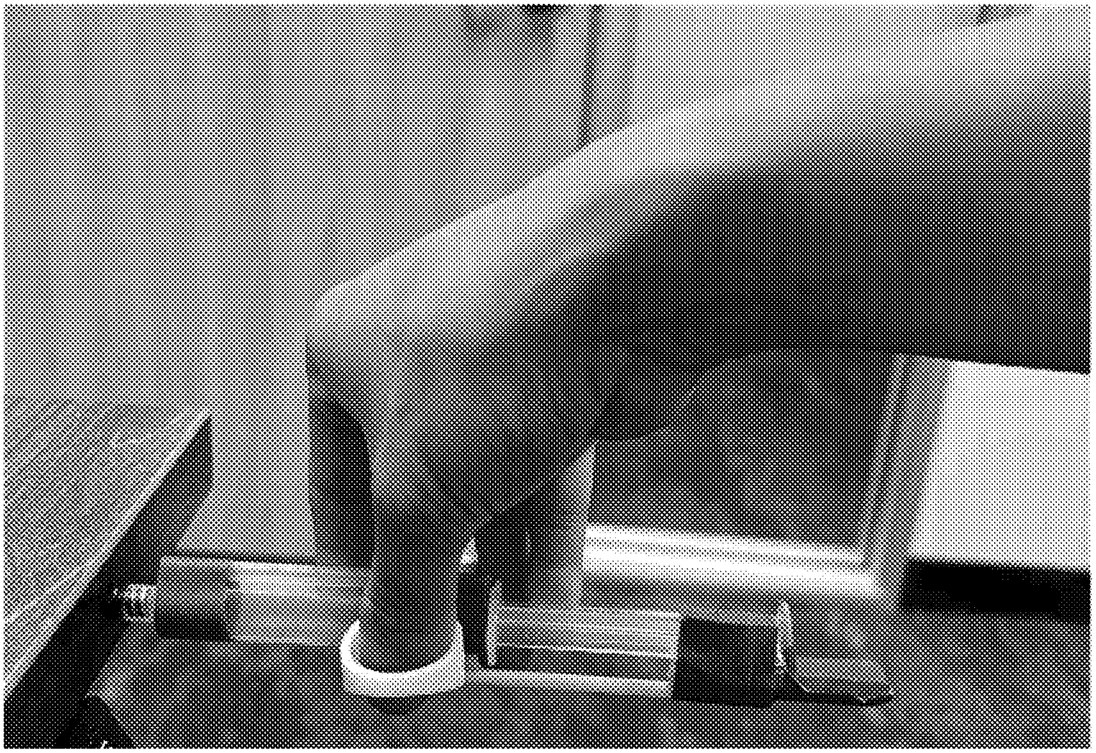

FIG. 12 shows a side view of said force sensor in simulated use, wherein the first lumen and the second lumen are adjacent to each other.

Figure 13:
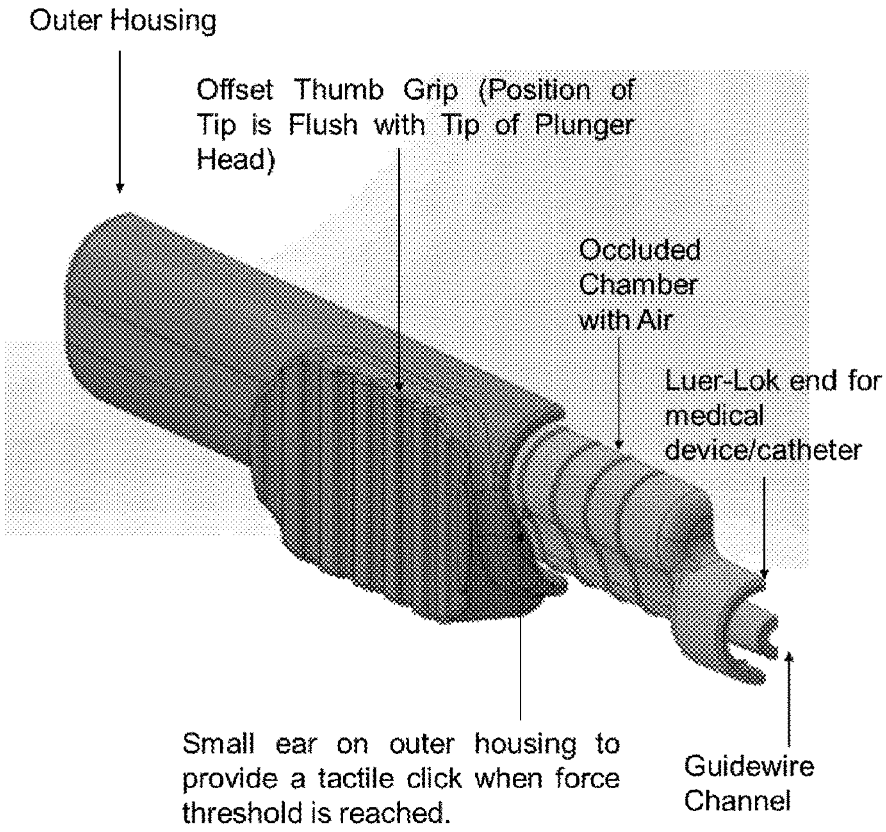

FIG. 13 shows an isometric front perspective view of another alternative embodiment of the force sensor of the present invention.

Figure 14:
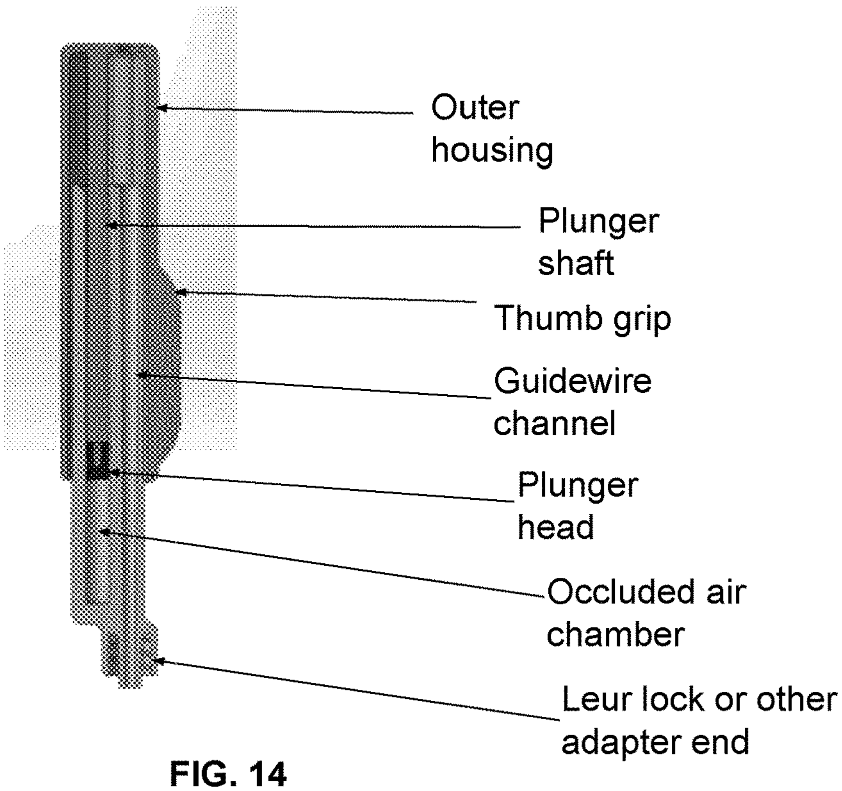

FIG. 14 shows a cutaway side view of the alternative embodiment of the force sensor.

Figure 15:
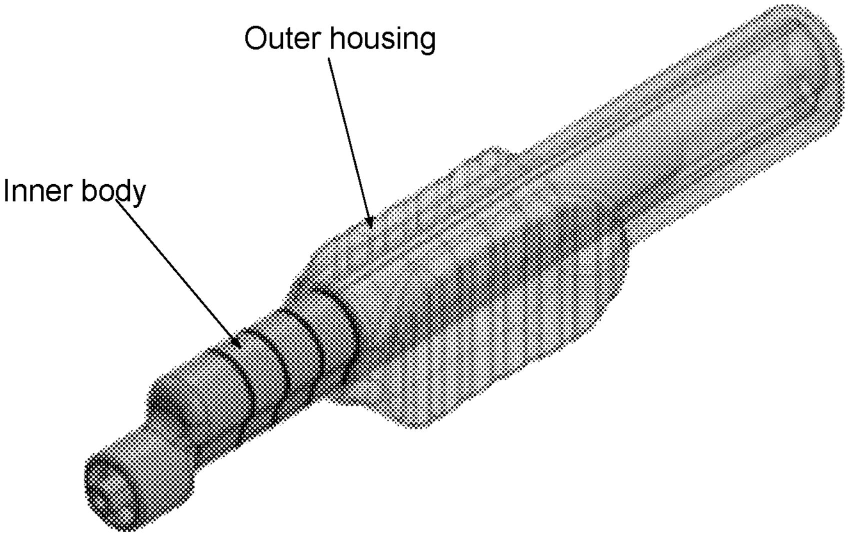

FIG. 15 shows a front isometric perspective view of said force sensor.

Figure 16:
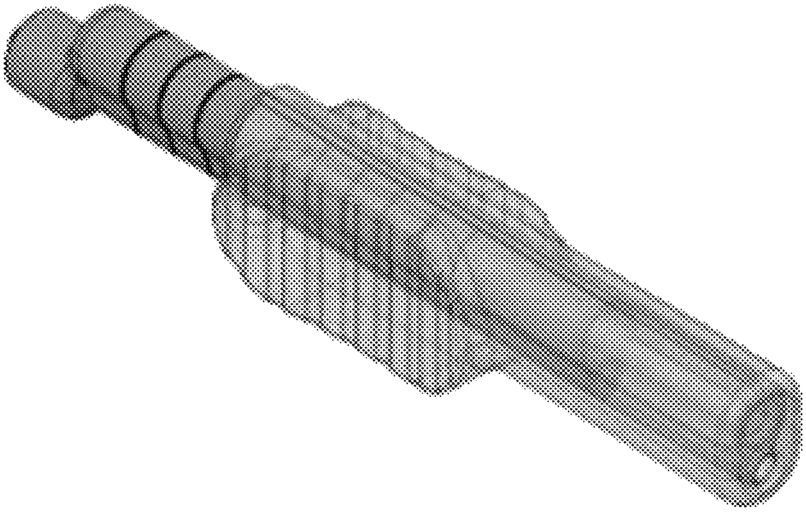

FIG. 16 shows a rear isometric perspective view of said force sensor.

Figure 17:
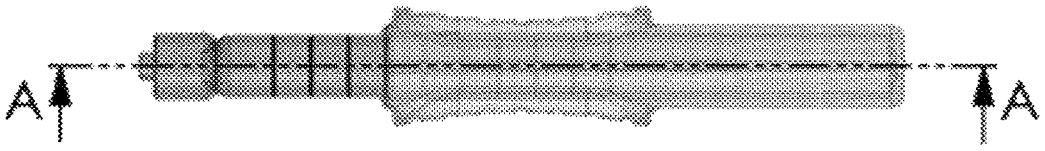

FIG. 17 shows a partially transparent, top view of said force sensor.

Figure 18:
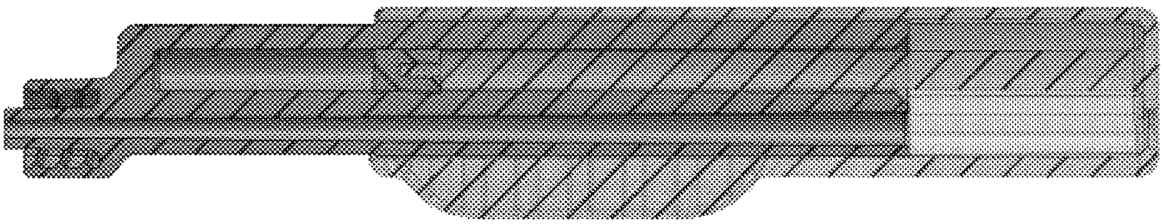

FIG. 18 shows a cutaway, side view of said force sensor.

Figure 19:
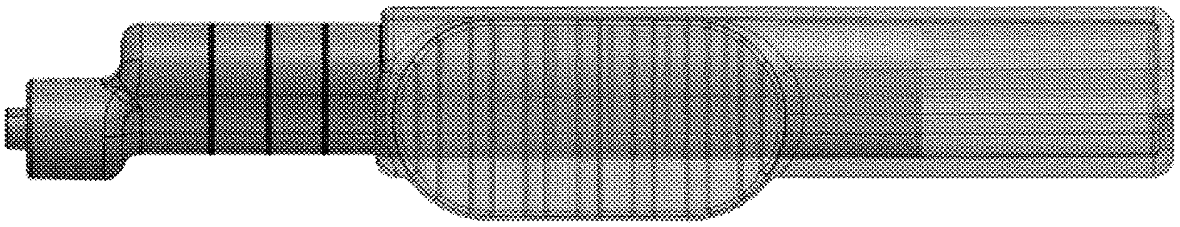

FIG. 19 shows a partially transparent, side view of said force sensor.

Figure 20A:
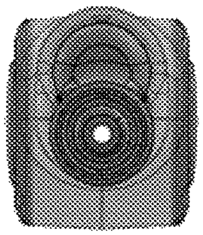

FIG. 20A shows a partially transparent, front view of said force sensor.

Figure 20B:
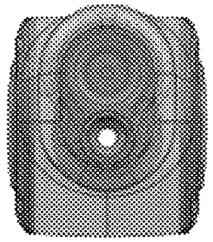

FIG. 20B shows a partially transparent, back view of said force sensor.

Figure 21A:
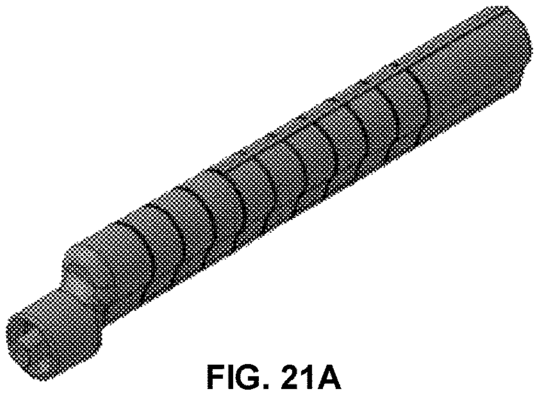

FIG. 21A is a front isometric perspective view of an internal body of said force sensor.

Figure 21B:
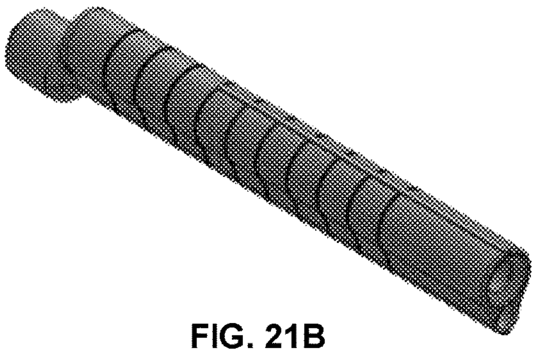

FIG. 21B shows a rear isometric perspective view of said internal body.

Figure 22A:
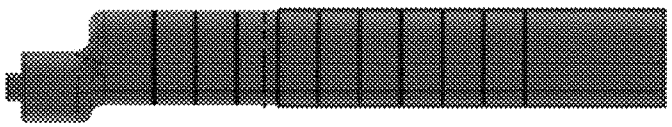

FIG. 22A shows a side view of said internal body. Vertical striped markings correspond to force levels, and in some embodiments, may be color-coded (e.g., red, yellow, green), indicating different risk levels to the patient. The vertical striped markings may also be embossed or recessed to provide tactile feedback at various displacements, which in some embodiments, may correspond to critical levels of force.

Figure 22B:
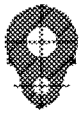

FIG. 22B shows a rear view of said internal body. Keyed grooves or keys on the dorsal and ventral portions may, in some embodiments, provide low friction alignment of various components of the force sensor. In some embodiments, the keyed grooves or keys may prevent rotation of various components of the force sensor.

Figure 23:
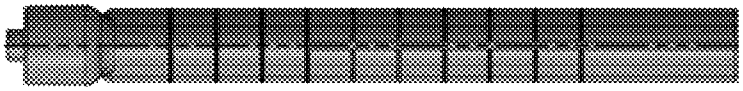

FIG. 23 shows a top view of said internal body.

Figure 24:
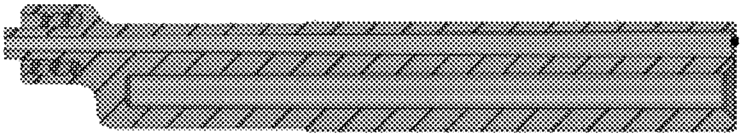

FIG. 24 shows a cutaway, side view of said internal body.

Figure 25:
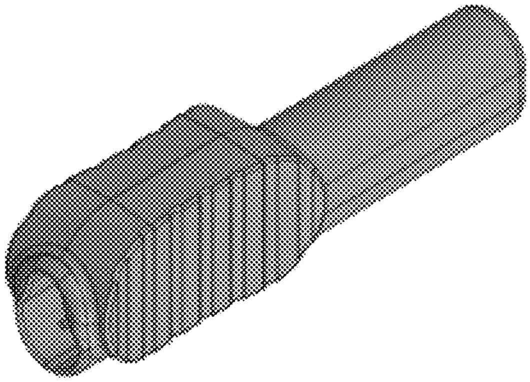

FIG. 25 shows a front isometric perspective view of an outer housing of said force sensor.

Figure 26:
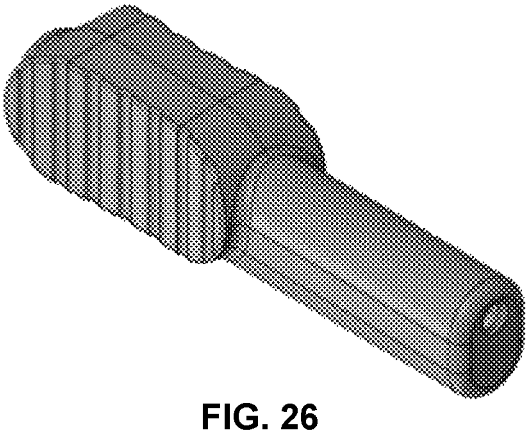

FIG. 26 shows a rear isometric perspective view of said outer housing.

Figure 27:
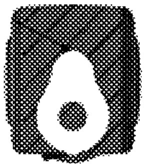

FIG. 27 shows a cutaway, front view of said outer housing.

Figure 28:
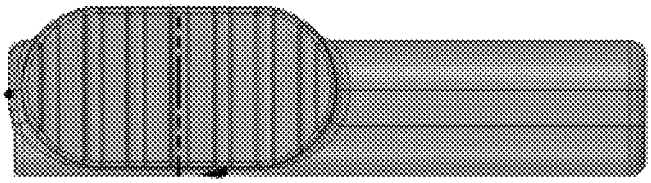

FIG. 28 shows a side view of said outer housing.

Figure 29:
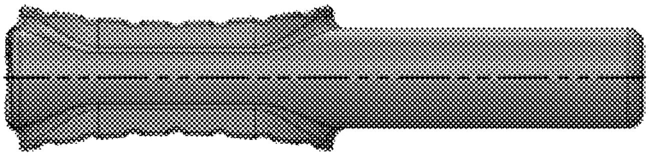

FIG. 29 shows a top view of said outer housing.

Figure 30:
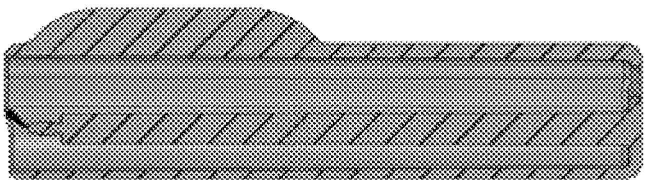

FIG. 30 shows a cutaway, side view of said outer housing.

Figure 31:
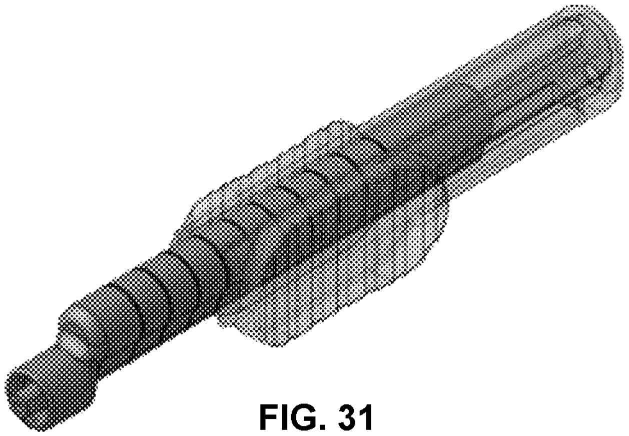

FIG. 31 shows a partially transparent, front isometric perspective view of another alternative embodiment of the force sensor of the present invention.

Figure 32:
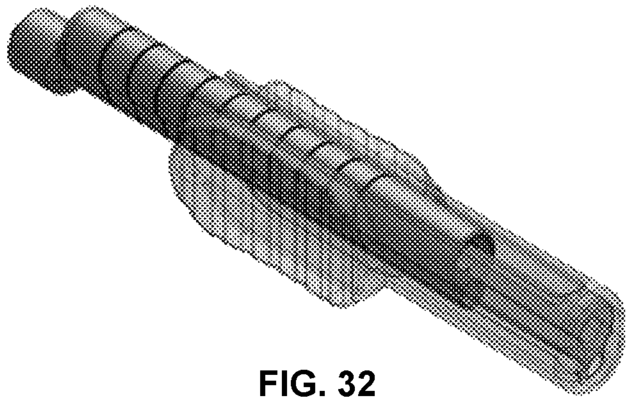

FIG. 32 shows a partially transparent, rear isometric perspective view of said force sensor.

Figure 33:
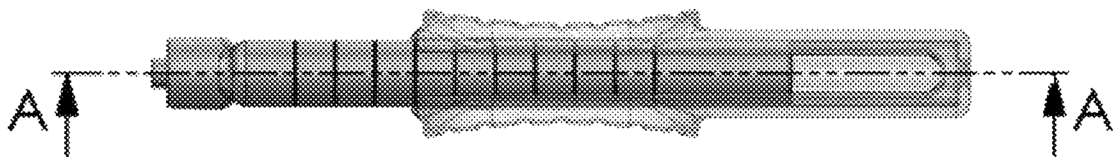

FIG. 33 shows a partially transparent, top view of said force sensor.

Figure 34:
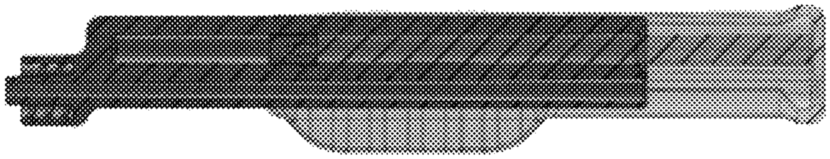

FIG. 34 shows a partially transparent, cutaway, side view of said force sensor.

Figure 35:
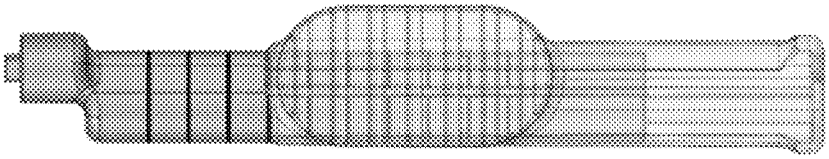

FIG. 35 shows a partially transparent, side view of said force sensor.

Figure 36A:
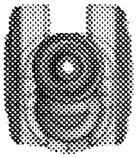

FIG. 36A shows a partially transparent, front view of said force sensor.

Figure 36B:
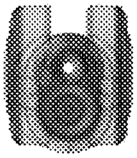

FIG. 36B shows a partially transparent, back view of said force sensor.

Figure 37:
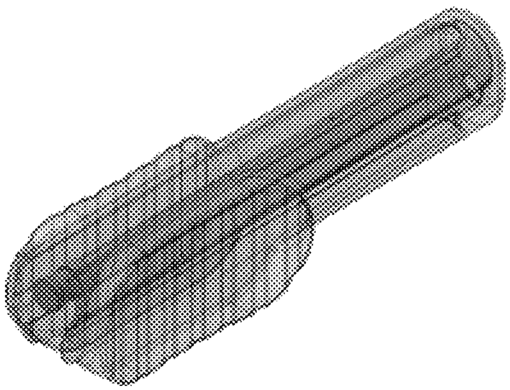

FIG. 37 shows a transparent, front isometric perspective view of an alternative embodiment of an outer housing of said force sensor.

Figure 38:
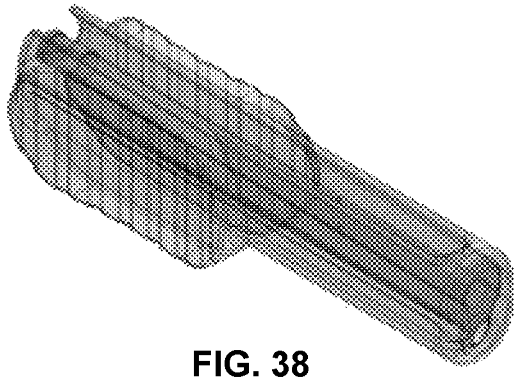

FIG. 38 shows a transparent, rear isometric perspective view of said outer housing.

Figure 39:
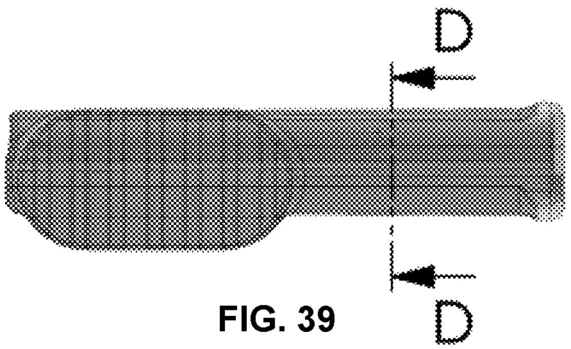

FIG. 39 shows a partially transparent side view of said outer housing.

Figure 40A:
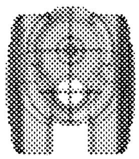

FIG. 40A shows a partially transparent, front view of said outer housing.

Figure 40B:
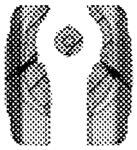

FIG. 40B shows a partially transparent, cutaway back view of said outer housing.

Figure 41:
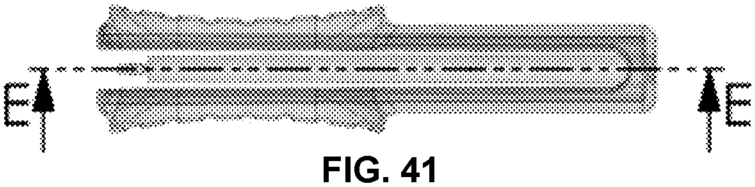

FIG. 41 shows a partially transparent, top view of outer housing.

Figure 42:
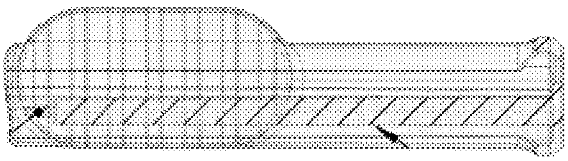

FIG. 42 shows a transparent side view of an alternative embodiment of said outer housing.

Figure 43:
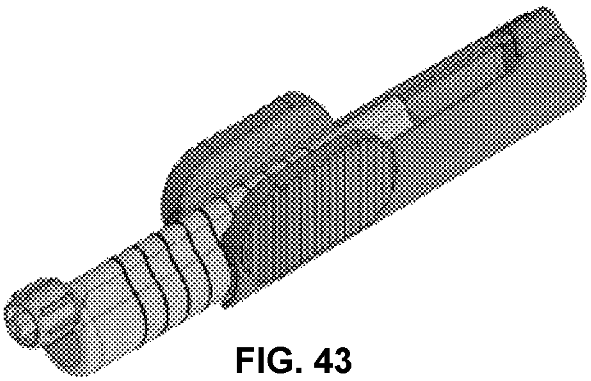

FIG. 43 shows a front isometric perspective view of a "winged" alternative embodiment of the force sensor of the present invention, wherein one or more offset thumb grips are disposed at least partially dorsal to at least a portion of an inner body of the force sensor.

Figure 44:
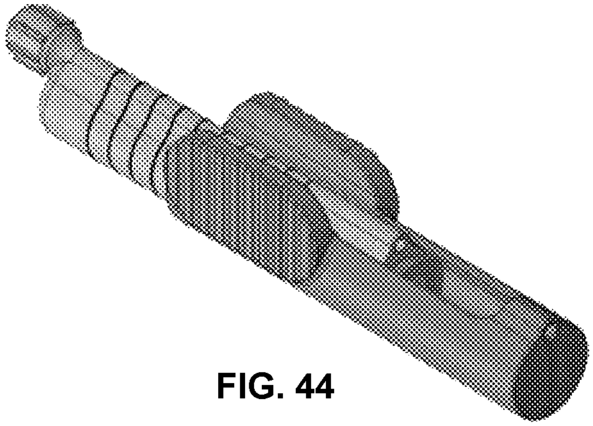

FIG. 44 shows a rear isometric perspective view of a winged alternative embodiment of said force sensor.

Figure 45:
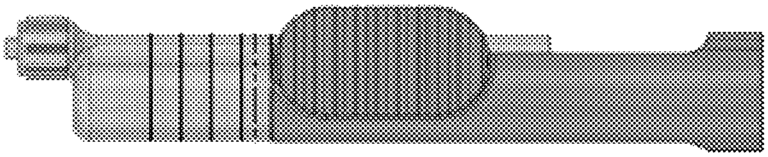

FIG. 45 shows a side view of a winged alternative embodiment of said force sensor.

Figure 46A:
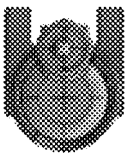

FIG. 46A shows a front view of a winged alternative embodiment of said force sensor.

Figure 46B:
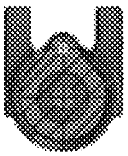

FIG. 46B shows a back view of a winged alternative embodiment of said force sensor.

Figure 47:
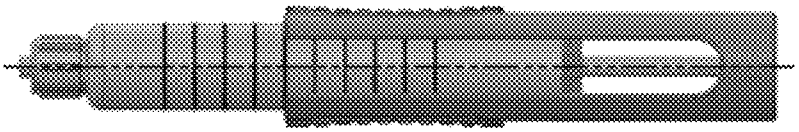

FIG. 47 shows a top view of a winged alternative embodiment of said force sensor.

Figure 48:
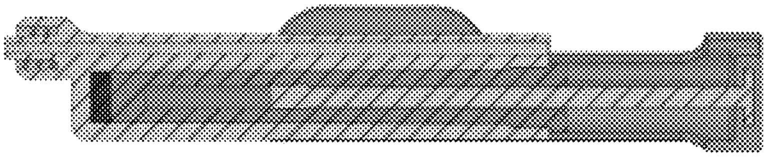

FIG. 48 shows a cutaway, side view of a winged alternative embodiment of said force sensor.

Figure 49A:
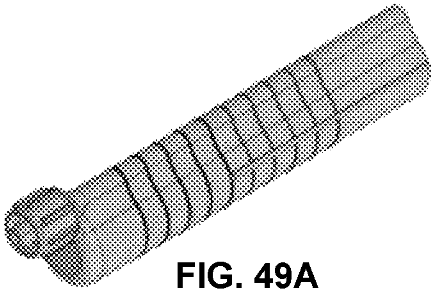

FIG. 49A is a front isometric perspective view of an internal body that may be adapted for use in a winged alternative embodiment of said force sensor.

Figure 49B:
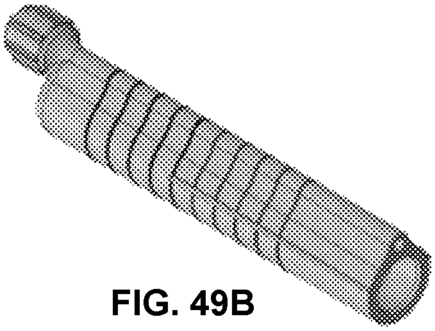

FIG. 49B shows a rear isometric perspective view of an internal body that may be adapted for use in a winged alternative embodiment of said force sensor.

Figure 50:
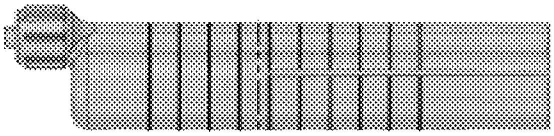

FIG. 50 shows a side view of said internal body that may be adapted for use in a winged alternative embodiment of said force sensor. Vertical striped markings correspond to force levels, and in some embodiments, may be color-coded (e.g., red, yellow, green), indicating different risk levels to the patient. The vertical striped markings may also be embossed or recessed to provide tactile feedback at various displacements, which in some embodiments, may correspond to critical levels of force.

Figure 51:
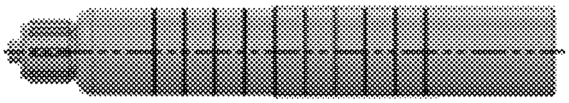

FIG. 51 shows a top view of said internal body that may be adapted for use in a winged alternative embodiment of said force sensor.

Figure 52:

FIG. 52 shows a cutaway, side view of said internal body that may be adapted for use in a winged alternative embodiment of said force sensor.

Figure 53A:
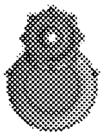

FIG. 53A shows a front view of said internal body that may be adapted for use in a winged alternative embodiment of said force sensor.

Figure 53B:
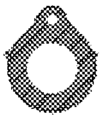

FIG. 53B shows a back view of said internal body that may be adapted for use in a winged alternative embodiment of said force sensor.

Figure 54A:
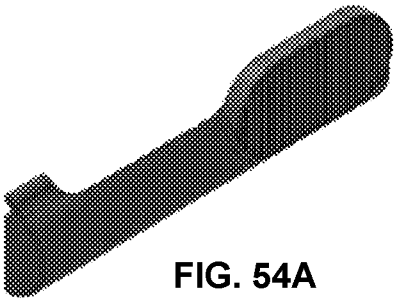

FIG. 54A shows a front isometric perspective view of an alternative embodiment of an outer housing that may be adapted for use in a winged alternative embodiment of said force sensor.

Figure 54B:
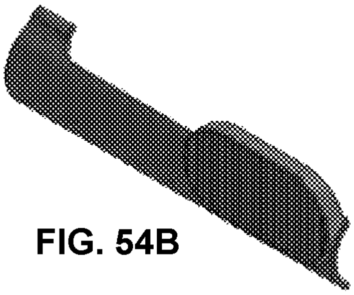

FIG. 54B shows a rear isometric perspective view of said outer housing that may be adapted for use in a winged alternative embodiment of said force sensor.

Figure 55:
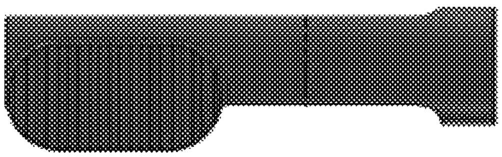

FIG. 55 shows a side view of said outer housing that may be adapted for use in a winged alternative embodiment of said force sensor.

Figure 56A:

FIG. 56A shows a partial front view of a winged alternative embodiment of said force sensor.

Figure 56B:
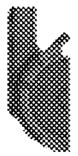

FIG. 56B shows a partial front view of a winged alternative embodiment of said force sensor.

Figure 57:

FIG. 57 shows a top view of one half of the outer housing of a winged alternative embodiment of said force sensor.

Figure 58:
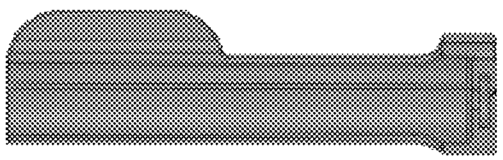

FIG. 58 shows a side view of an alternative embodiment of said outer housing of a winged alternative embodiment of said force sensor.

Figure 59:
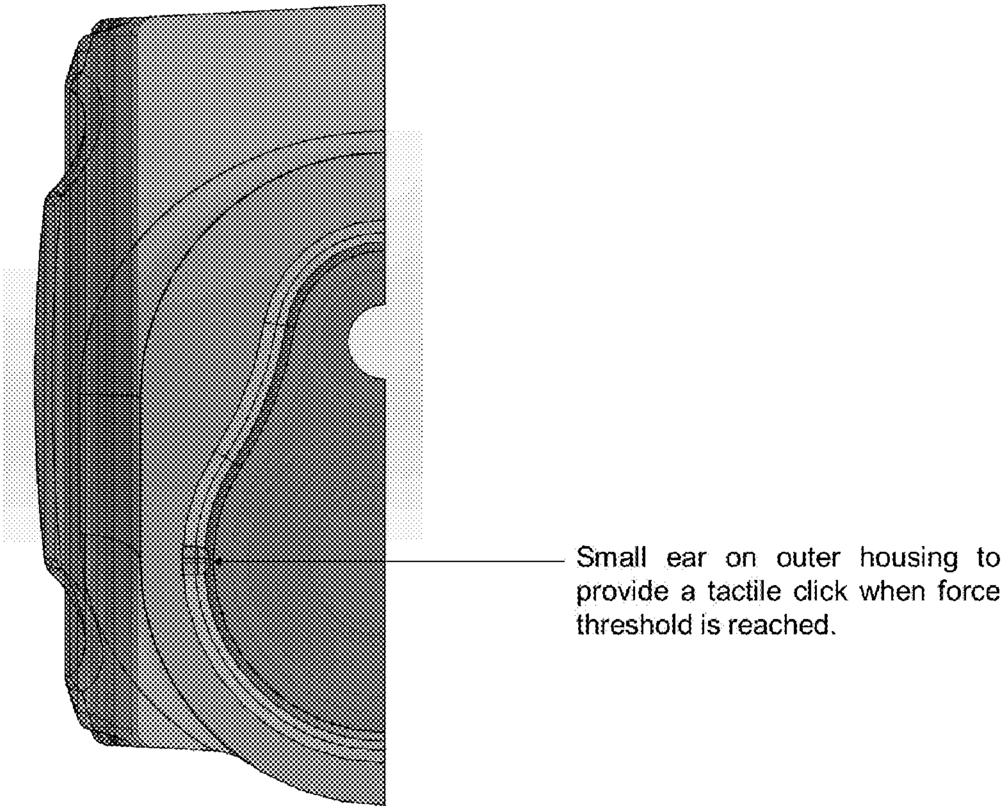

FIG. 59 shows a partial front view of the force sensor.

Figure 60:
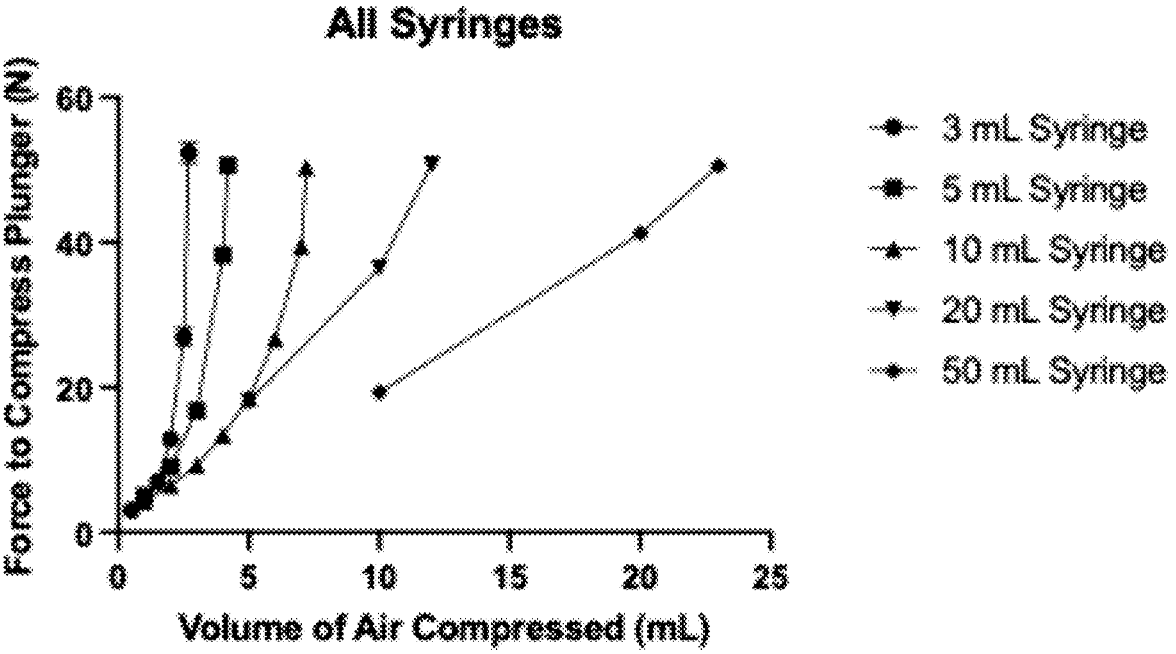

FIG. 60 shows the results of force required to compress a syringe plunger versus the volume of compressed air for syringes sized 3 mL, 5 mL, 10 mL, 20 mL, and 50 mL.

Figure 61:
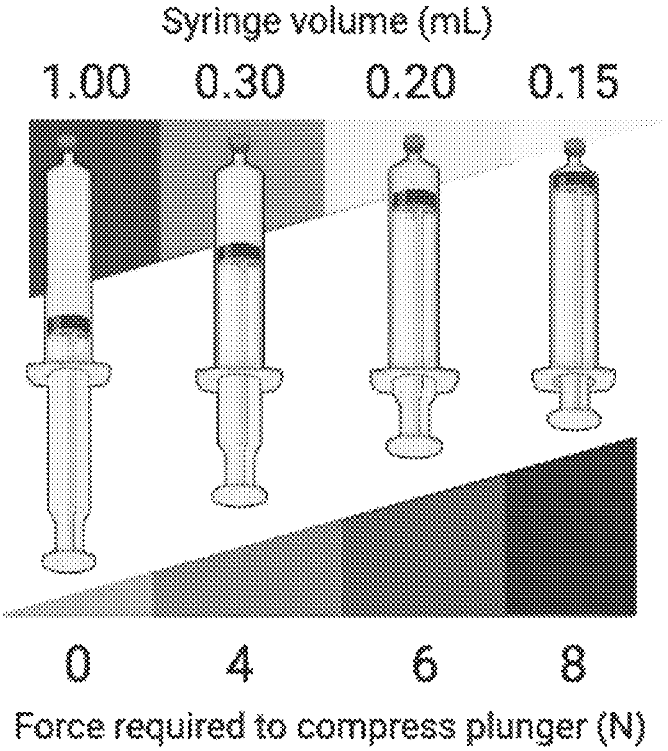

FIG. 61 shows the force required to compress the plunger (in Newtons) corresponding to the volume (in milliliters) of air in the lumen of a 1 mL syringe. Volume to push the syringe plunger to reach forces of 4 N (0.30 mL), 6 N (0.20 mL), and 8 N (0.15 mL) using an occluded 1.0 mL BD Luer-Lok™ syringe with the plunger starting at 1.0 mL.

Figure 62:
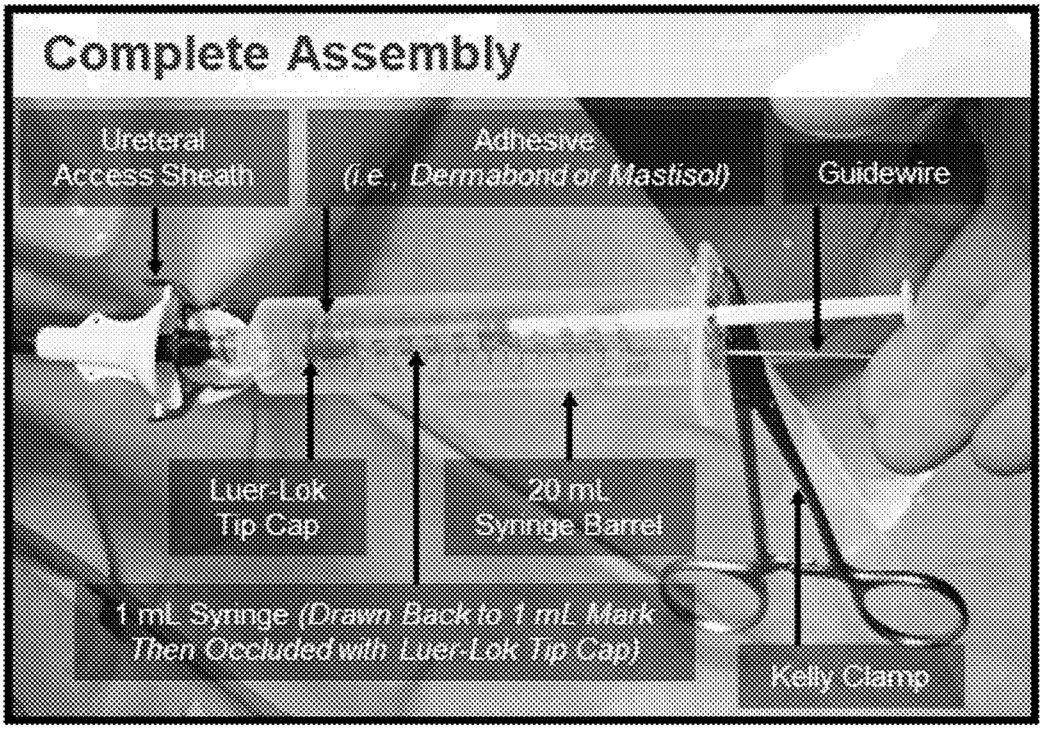

FIG. 62 shows an alternative embodiment of the present invention. An occluded 1.0 mL syringe (BD Luer-Lok™) placed within the barrel of a 20 mL syringe, connected to the obturator of a UAS. The guidewire passes alongside the 1 mL syringe through the 10 ml syringe barrel.

FIG. 63 shows multiple paired independent-samples F-tests comparing the standard deviations between the compressed volume readings of the 3 syringes brands (Luer-Lok™ syringe, Tuberculin syringe, Luer Slip syringe) at the 3 different force thresholds (4 N, 6 N, 8 N).

DETAILED DESCRIPTION OF THE INVENTION

All references, publications, and patents cited herein are incorporated by reference in their entirety as though they are fully set forth. Unless defined otherwise, technical, and scientific terms used herein have the same meaning as commonly understood by one of ordinary skill in the art to which this invention belongs. Hornyak, et al., Introduction to Nanoscience and Nanotechnology, CRC Press. (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, the Inventors have developed a novel medical device that is useful during surgery or medical procedures. In one embodiment, the device may be used for assisting and training surgeons by measuring force during ureteral access sheath deployment in urological surgeries, but applicable to catheter and sheath insertion for urological, surgical, laparoscopic, robotic, and vascular procedures. In one embodiment, the device is a force measurement device for catheter and sheath insertion procedures.

A force of less than 4 N results in no clinically visible ureteral injury. (post-ureteroscopic lesion score (PULS) of 0 or 1)), which translates into a safe threshold that should not require a ureteral stent placement in uncomplicated cases as it indicates that post ureteroscopic ureteral edema is unlikely. A force of 6 N was determined to be a threshold below which no high-grade ureteral injury occurred (i.e., splitting of the urothelium—a PULS 3 or higher). At a force of 8 N or more, PULS 3 level injuries have been noted in upwards of 20% of cases.

Referring now to FIGS. 1-8, in some embodiments, the present invention features a device to measure force as well as methods of using said device. Devices described herein may be used to measure the force applied during the passage of any catheter, needle, trocar, or other assembly into the tissues of the human body or during surgical dissection with regard to the amount of force being exerted on a nerve, blood vessel, or other sensitive tissue during surgical retraction.

According to some embodiments, the present invention features a force-sensing device (100). In some embodiments, the force sensing device (100) may comprise a tube (110), a plunger (120), and an outer casing (130). In some embodiments, the tube (110) comprises a first end (111), a second end (112), a first lumen (115), and a second lumen (117) disposed within the first lumen (115). The first end (111) of the tube (110) may comprise an opening (128) through which the plunger (120) may pass through. In certain embodiments, the plunger (120) directly contacts the inner edge of the first lumen (115) as well as the outer portion of the second lumen (117) to create an essentially airtight seal. Additionally, in some embodiments, the second end (112) of the tube (110) is occluded, thus creating an airtight first lumen (115). In preferred embodiments, the first lumen (115) is airtight. In some embodiments, the plunger (120) is slidably coupled to the second lumen (117) and may comprise a first plunger end (121) and a second plunger end (122) having a handle (128) disposed thereon. The plunger (120) may further comprise a plunger lumen (125) disposed through the first plunger end (121) to the second plunger end (122). In some embodiments, the plunger lumen (125) extends through the handle (128), with the plunger lumen (125) and the second lumen (117) of the tube (110) being fluidly coupled, allowing a guidewire to pass through both lumens. In other embodiments, the plunger lumen (125) extends only to the interior surface of the handle (128), without passing through it. While the plunger lumen (125) and the second lumen (117) of the tube (110) are still fluidly coupled, a guidewire cannot be passed through this configuration. Lastly, the outer casing (130) may be disposed over at least a portion of the tube (110) and at least a portion of the plunger (120). In some embodiments, the outer casing (130) comprises a first casing end (131), a second casing end (132), and a lumen (135). The first casing end (131) and the second casing end (132) may both comprise an opening (e.g., a first opening (138) and a second opening (139), respectively) for accessing the lumen (135).

In some embodiments, the first lumen (115) comprises a fluid therein. For example, in some embodiments, when the handle (128) of the plunger (120) is pushed towards the first end (111) of the tube (110), the plunger (120) compresses the fluid within the first lumen (115) of the tube (110), and the compression of the fluid corresponds to an applied force. In certain embodiments, the device (100) is a pneumatic device, and the first lumen (115) comprises a gas (e.g., air; e.g., a mixture mainly of oxygen and nitrogen) therein. Thus, in some embodiments, when the handle (128) of the plunger (120) is pushed towards the first end (111) of the tube (110), the plunger (120) compresses the gas within the first lumen (115) of the tube (110) and the compression of the gas corresponds to an applied force. In other embodiments, the device (100) is a hydraulic device, and the first lumen (115) comprises a liquid therein. Thus, in some embodiments, when the handle (128) of the plunger (120) is pushed towards the first end (111) of the tube (110), the plunger (120) compresses the fluid within the first lumen (115) of the tube (110) and the compression of the liquid corresponds to an applied force.

In some embodiments, the second lumen (117) is centrally disposed within the first lumen (115) of the tube. In some embodiments, the second lumen (117) is a guidewire lumen through which a guidewire may be passed therethrough. In alternative embodiments, the tube (110) comprises a first lumen (115) and a second lumen (117) where the first lumen (115) and the second lumen (117) are adjacent to each other.

In some embodiments, the second lumen (117) is a guidewire lumen through which a guidewire may be passed therethrough, wherein the second lumen (117) is adjacent to the first lumen (115). In some embodiments, the force sensor (100) may further comprise one or more grips to facilitate manual use of said force sensor (100). In some embodiments, said grips may be ring-shaped grips adapted to accommodate a user's fingers.

In some embodiments, the present invention may comprise an outer housing, an inner body, and one or more offset thumb grips, or combinations thereof. In some embodiments, the present invention may feature an offset thumb grip on one or more sides of the force sensor (100). In other embodiments, the present invention may comprise a unitary body, wherein the unitary body comprises at least a portion of the structures that comprise the outer housing and the inner body.

In some embodiments, the outer housing may comprise one or more offset thumb grips. In some embodiments, the outer housing may further comprise a small "ear," wherein the ear provides a tactile click, a noise, tactile feedback, haptic feedback, or combinations thereof, when one or more force thresholds are reached.

In some embodiments, the inner body may further comprise a first lumen (115), a second lumen (117), a guidewire lumen, a guidewire channel, or combinations thereof. In some embodiments, the guidewire channel and/or guidewire lumen may be the second lumen (117). In some embodiments, the guidewire channel and/or guidewire lumen may be discrete, separate lumens. In some embodiments, the inner body may further comprise an interface for a medical device. In some embodiments, the interface for a medical device may be disposed on a distal end of the inner body. In some embodiments, the interface for a medical device may comprise a Luer-Lock style interface. In certain other embodiments, the interface is a pressure fitting interface, a Luer Slip style interface, a Tuberculin style interface, or a twist-to-connect coupling interface. In some embodiments, the inner body may further comprise a plunger shaft, a plunger head, or an occluded air chamber.

In some embodiments, the present invention may comprise a guidewire channel, a plunger shaft, a plunger head, or an occluded air chamber. In some embodiments, the guidewire channel may be the second lumen (117).

In some embodiments, the outer casing (130) is cylindrical. In some embodiments, the outer casing is rectangular.

In some embodiments, the second end (112) of the tube (110) further comprises an interface for a medical device. In certain embodiments, the interface is a Luer-Lock style interface. In certain other embodiments, the interface is a pressure fitting interface, a Luer Slip style interface, a Tuberculin style interface, or a twist-to-connect coupling interface. In some embodiments, the interface is positioned at a distal end of a medical device.

Non-limiting examples of medical devices include, but are not limited to, a ureteral access sheath (UAS), an endoscope, a ureteroscope, a Foley catheter, or an intravenous line. For example, the present invention may be used to pass up a ureteroscope so excessive force was not exerted. In other applications, it could be used when passing a Foley catheter into the bladder, an intravenous line into a vein, or any endoscope being passed into any organ in the body.

In some embodiments, the devices described herein further comprise indicators (e.g., visual indicators) to alert the users as the input force increases. In some embodiments, the visual indicators comprise a green visual indicator, a yellow visual indicator, a red visual indicator, a black visual indicator, or a combination thereof. In some embodiments, a green visual indicator indicates 4 N of force being applied. In some embodiments, a yellow visual indicator indicates 6 N of force being applied. In some embodiments, a red visual indicator indicates 8 N of force being applied. In some embodiments, a black visual indicator corresponds to 9N of force being applied. Various colors may be used as visual indicators in accordance with the devices described herein.

In other embodiments, the devices described herein provide visual indicators at three predefined force thresholds (e.g., 4 N, 6 N, 8 N). In alternative embodiments, the devices described herein may only. provide an indication when 6 N is applied to the UAS. In other embodiments, the predefined force thresholds may be indicated by transmission of an electrical signal or by a tactile appreciated detent.

Without wishing to limit the present invention to any theories or mechanisms, it is believed that alerting a surgeon to 6 N of force allows for safe passage of the UAS (even up to 16Fr). An 8 N indicator alerts a surgeon to a hard stop because a force at that level will result in injury in upwards of one-fifth of cases that require a ureteral stent to be left in place for 2-6 weeks, and risks the development of a long-term ureteral stricture in upwards of 13% of patients. The proposed device would enable the surgeon to avoid any injury to the ureter by adhering to a 6 N threshold. Further, for UAS placed at the 4 N force threshold, surgeons may be able to safely eliminate ureteral stent placement after ureteroscopy; this alone would decrease the attendant morbidity and cost of ureteroscopic stone removals.

In some embodiments, a user is capable of continuously measuring input force in real time during the deployment of the surgical device in a patient.

In some embodiments, the force-sensing device (100) is a handheld device, while in other embodiments, it is integrated with robotics.

In some embodiments, the devices described herein may be made of plastic or metal. In other embodiments, devices derived herein made of plastic may be end-mounted (i.e., the device is directly in line with the UAS or catheter) or side-mounted. In other embodiments, devices derived herein made of metal may be end-mounted or side-mounted.

In some embodiments, the devices described herein may undergo gas sterilization. In some embodiments, the devices described herein are single-use, disposable, or sterilizable reusable items. In some embodiments, the internal portion of the device is hollow to allow the passing of a guidewire through the device. In some embodiments, the sliding portion of the device is isolated with linear bearings providing smooth sliding motion.

In some embodiments, the devices described herein allow for measurement of the catheter sheath deployment/insertion force via an end-mounted or side-mounted fluid-power system mechanism (i.e., either a pneumatic mechanism or a hydraulic mechanism). In certain embodiments, fluid displacement is used as the primary method of force measurement. Displacement of 0 to maximum range would correspond to an applied force of 0 to 8 N. In one embodiment, the plunger at the maximum range may stop prior to reaching the bottom of the syringe. In another iteration, the plunger at the maximum range could also be to the bottom of the syringe. In other embodiments, an internal spring may be used as the primary method of force measurement.

The present invention may further include a method of utilizing the force-sensing device (100) as described herein to monitor the insertion force of a medical device during a surgical procedure on a patient. In some embodiments, the method comprises attaching a force sensing device (100) as described herein to a medical device and inserting the medical device into the patient. In some embodiments, the force sensing device (100) monitors and outputs the force value during the medical device insertion. For example, when the handle (128) of the plunger (120) is pushed towards the first end (111) of the tube (110) during the insertion of the medical device into the patient, the plunger (120) compresses a fluid within the first lumen (115) of the tube (110), wherein the compression of the fluid corresponds to an applied force.

In other embodiments, the present invention may comprise a method of utilizing the force-sensing device (100) as described herein to monitor the force of a medical device during a surgical procedure on a patient. In some embodiments, the method comprises attaching a force sensing device (100) as described herein to a medical device and manipulating the medical device into the patient. In some embodiments, the force sensing device (100) is attached to the medical device as it is being advanced into a hollow organ or through the skin of a patient. In some embodiments a force sensor (100) may be attached to a tip or an end of a Foley catheter in order to monitor the force applied to the Foley catheter so as not to injure the urethra. In some embodiments, a force sensor (100) may be applied to a tip or a back end of an endoscope. In some embodiments, said endoscope may be used for bronchoscopy, colonoscopy, or other endoscopy procedures.

In some embodiments, the force sensing device (100) may be applied on a needle to monitor the force applied as the needle penetrates the patient's skin or vein. In some embodiments, the force sensor (100) is calibrated or otherwise adapted to monitor the amount of force that would need to be applied depending on the particular site of intended use, for example, to avoid perforation of a patient's colon, urethra, or similar organ or body structure. In some embodiments, a safe force is defined for a specific organ or body structure, and the force sensor (100) is accordingly adapted to indicate when an operator using the force sensor (100) is approaching that limit of safe force. In some embodiments, the force sensing device (100) monitors and outputs the force value during the medical device manipulation. For example, when the handle (128) of the plunger (120) is pushed towards the first end (111) of the tube (110) during the manipulation of the medical device into the patient, the plunger (120) compresses a fluid within the first lumen (115) of the tube (110), wherein the compression of the fluid corresponds to an applied force.

In one embodiment, sterile procedures are used during the use process. In some embodiments, the medical device is a device used in an endoscopic, laparoscopic, robotic, and/or minimally invasive surgical procedure. In one embodiment, the medical device is a ureteral access sheath. In one embodiment, the force sensing device is a handheld device. In one embodiment, the force sensing device further comprises visual indicators to alert the user as the input force increases. In some embodiments, the force sensing device further comprises tactile indicators or auditory indicators to alert the user as the input force increases.

Example 1

The following is a non-limiting example of the present invention. It is to be understood that said example is not intended to limit the present invention in any way. Equivalents or substitutes are within the scope of the present invention.

Given the clinical findings that 8 N was a threshold of crucial importance during UAS insertion, Boyle's Law was applied to estimate the amount of compression necessary in an occluded 1 mL syringe to reach 8 N; the amount of compression to reach forces of 4 N and 6 N was also defined. The latter information was sought because if the UAS is placed with a force of 4 N or less, then the impact on the ureteral wall is minimal, and thus, placement of an indwelling ureteral stent at the end of the procedure may not be necessary. Further, a force of 6 N is routinely applied to place a larger access sheath, as this force is considered safe and enables the placement of a larger sheath than would be possible with the application of only 4 N to the UAS.

The following example documents a series of benchtop tests using the UCI-FS to calibrate several 1 mL occluded syringes from different manufacturers to determine the reproducibility of both inter-syringe and intra-syringe volumes corresponding to 4 N, 6 N, and 8 N. In addition, instructions were included on how to assemble a force sensor in the operating room from materials readily available therein.

Materials and Methods

All brands of 1 mL medical-grade syringes available at the University of California, Irvine Medical Center operating room, outpatient surgical center, anesthesia preoperative clinic, anesthesia pain clinic, urology clinic, and inpatient wards were collected for evaluation. In total, three brands of syringes were identified, including the 1 mL Luer-Lok™ Syringe (Becton Dickinson, Franklin Lakes, NJ), 1 mL Tuberculin Syringe (Becton Dickinson, Franklin Lakes, NJ), and 1 mL Luer Slip Syringe (Berpu Medical Technology, Zhejiang, China). A 1 mL insulin syringe (Becton Dickinson, Franklin Lakes, NJ) was excluded due to the presence of a pre-packaged needle that could not be removed from the syringe.

Figure 1:
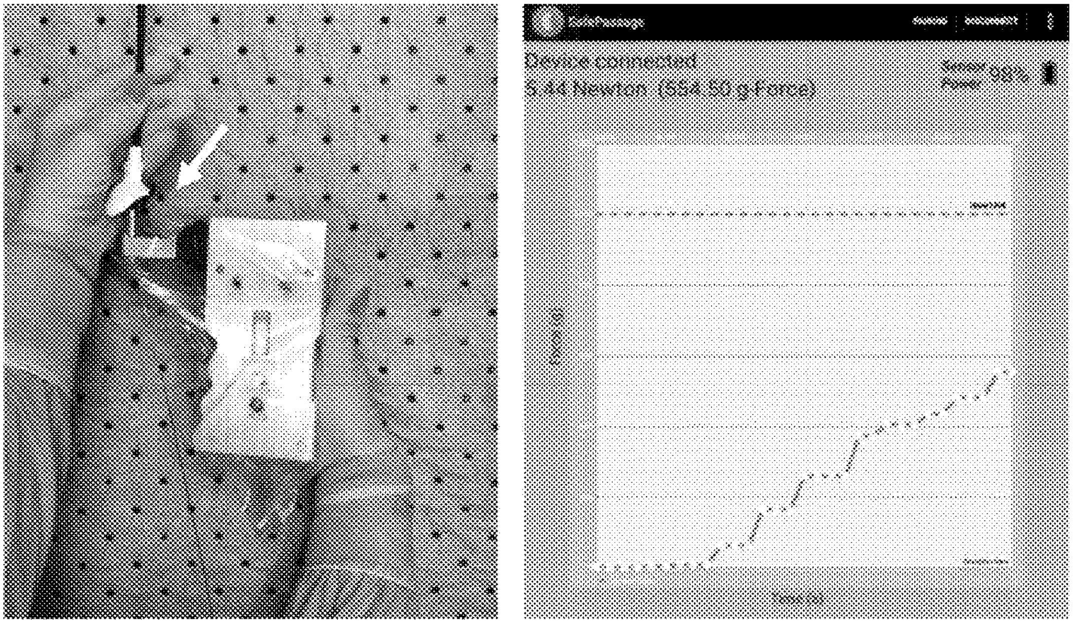
FIG. 1 shows the proprietary mechanical UAS force sensor connected to a UAS with a screenshot of sample force reading.
Figure 2:
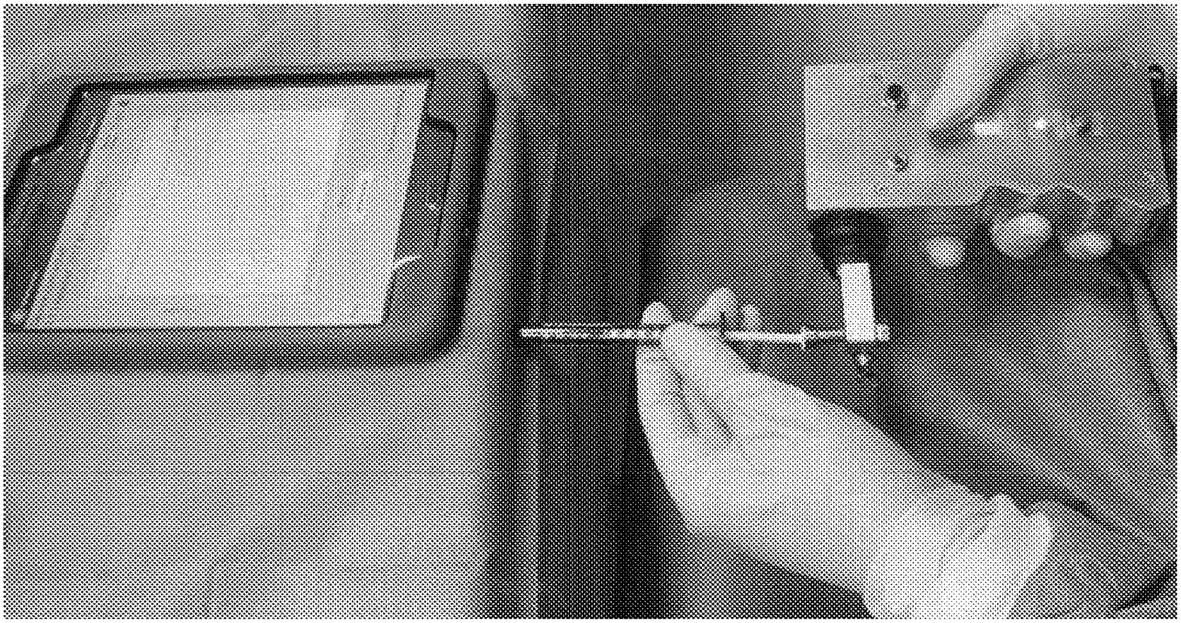
FIG. 2 shows the experimental set-up testing the relationship between applied force and the change in volume of an occluded 1 ml syringe with the UCI-FS.

The UCI-FS was first calibrated with a set of standardized tungsten weights to ensure its accuracy and precision to 0.01 N. Each 1 mL syringe was occluded with the plunger at the 1 mL marking by sealing the tip with a BD Luer Tip Cap (Becton Dickinson, Franklin Lakes, NJ). Five of each brand of syringe were tested for five trials each by using the UCI-FS to push the occluded syringe against a flat surface (FIG. 2). The volume on each syringe at 4 N, 6 N, and 8 N of force was recorded for a total of 225 data points. To minimize observer bias, testing was performed by two fully trained urological surgeons.

Continuous variables were displayed as mean and standard deviation. For each force threshold (i.e., 4 N, 6 N, and 8 N) and syringe brand (i.e., Luer-Lok™, Tuberculin, Luer Slip), analysis of variance (ANOVA) Tukey post-hoc analysis was employed to assess the consistency of each syringe's final volume in assessing the insertion force. All statistical analysis was performed using IBM SPSS Statistics, Version 29.0 (IBM Corp., Armonk, NY). Graphs were generated using GraphPad Prism Version 10.0.1 for MacOS, GraphPad Software, Boston, Massachusetts, USA.

Figure 3:
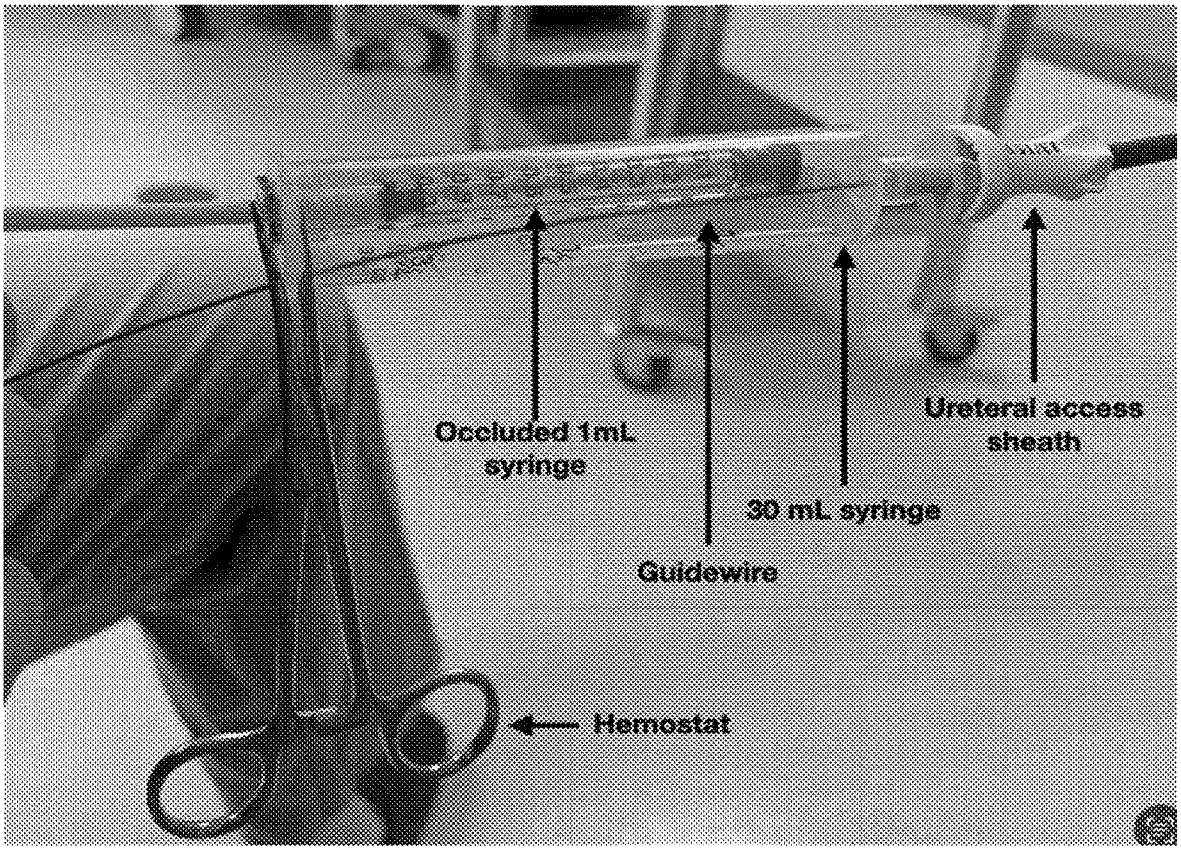
FIG. 3 shows a labeled set-up of an air force sensor over a guidewire attached to a ureteral access sheath.
Figure 4:
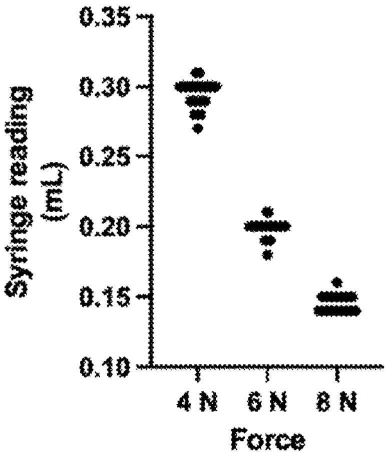
FIG. 4 shows benchtop testing of the air force sensor with our validated UCI force sensor using an occluded 1 mL syringe (Becton Dickinson, model number 43237-2).

To move this device into the clinical realm a very simple set-up has been devised. A 1 mL Luer-Lok™ Syringe was occluded with a BD Luer Tip Cap and Dermabond or Mastisol liquid adhesive. The 1 mL Luer-Lok™ Syringe is then clamped with a short Kelly clamp to the outer portion of a 20 mL Luer-Lok™ Syringe (Becton Dickinson, Franklin Lakes, NJ). The end of the larger syringe can then be passed over the guidewire over which the UAS has been passed and then attached to the obturator end of the UAS. The surgeon supports the UAS with one hand and then places constant pressure on the 1 mL syringe with the other hand until 0.2 mL is reached, indicating 6 N of force. All components are available in the operating room and take less than 30 seconds to set up (FIG. 3).

Results

Figure 5:
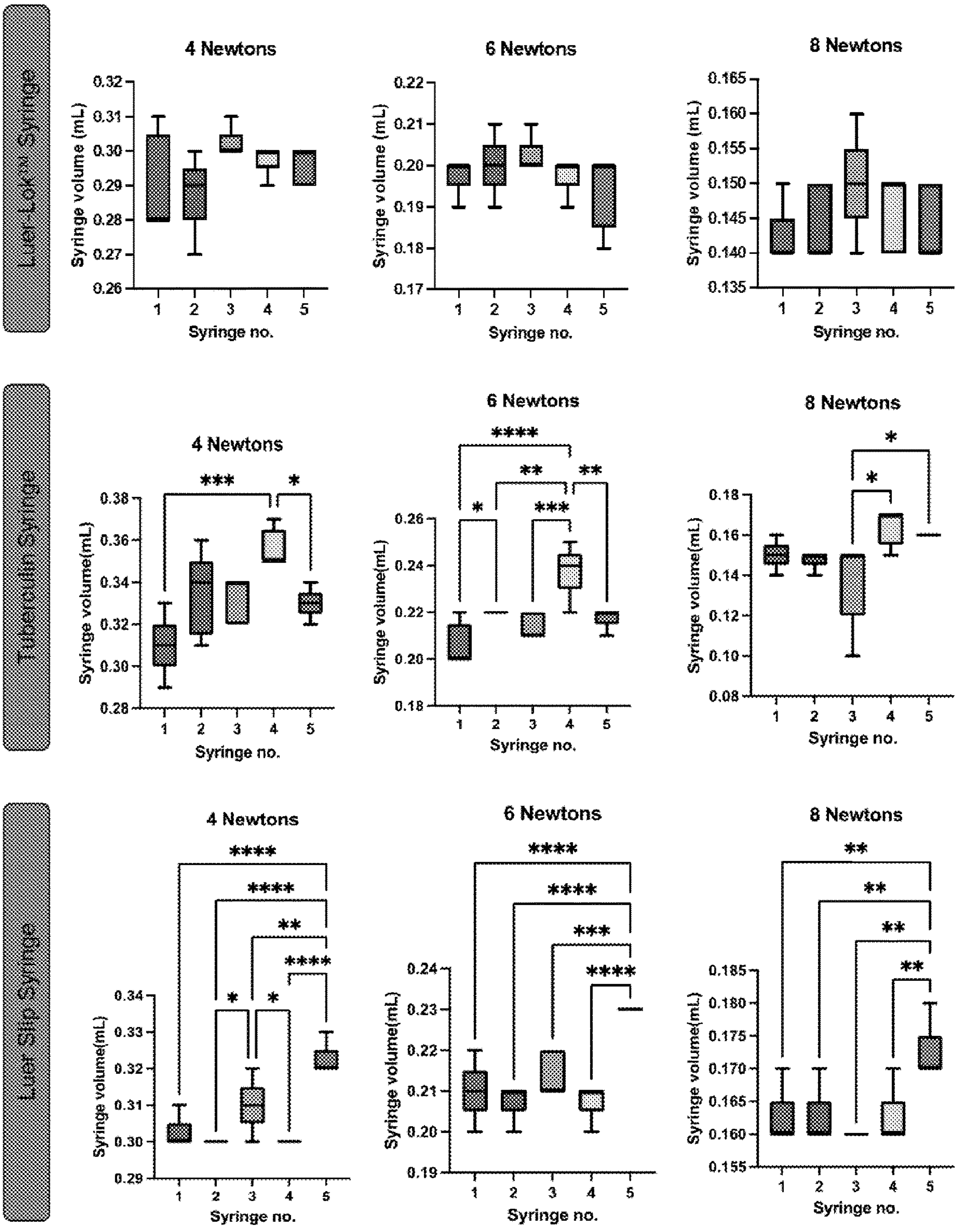
FIG. 5 shows analysis of variance comparison (ANOVA) and Tukey post-hoc analysis of the compressed syringe volumes between the three different syringe brands (Luer Lock™, Tuberculin, Luer Slip) at the three different force thresholds (4 N, 6 N, 8 N). Note: ns=P>0.05; *=P≤0.05; =P≤0.01; *=P≤0.001; ****=P≤0.0001 (For the last two choices only).
Figure 6A:
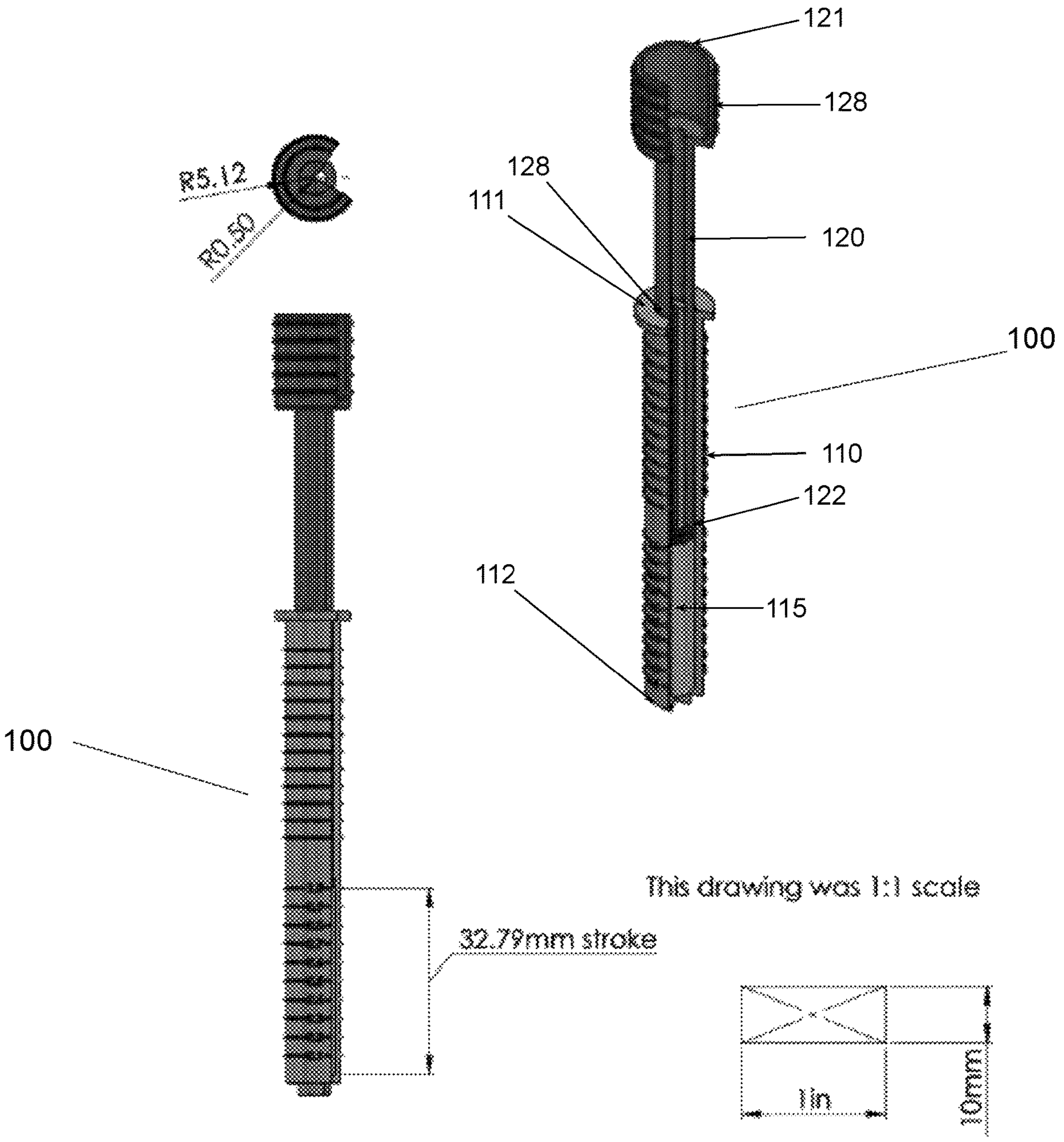
Figure 6B:
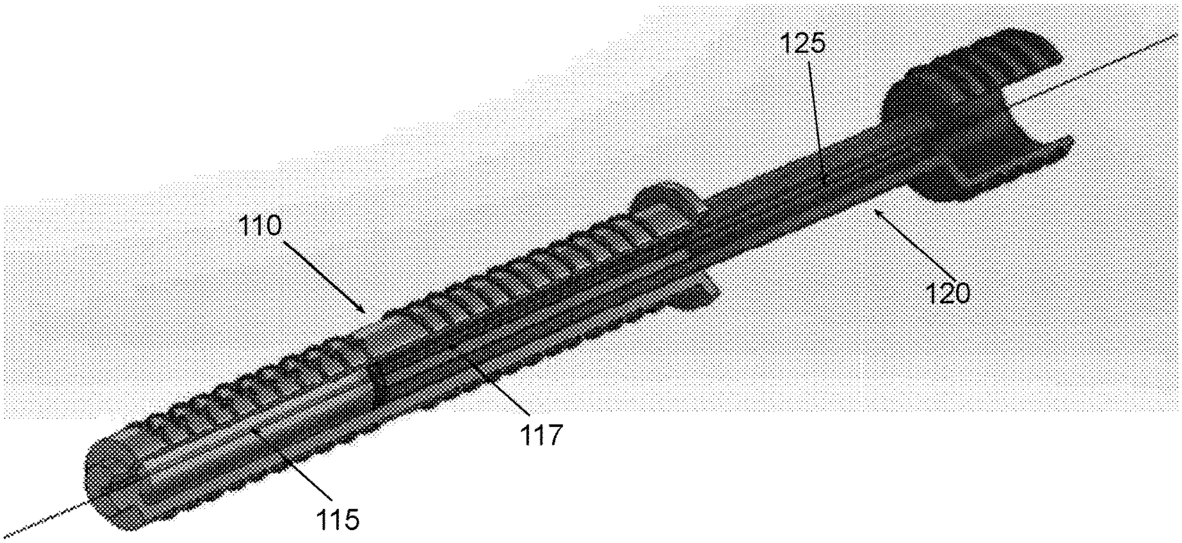
Figure 6C:
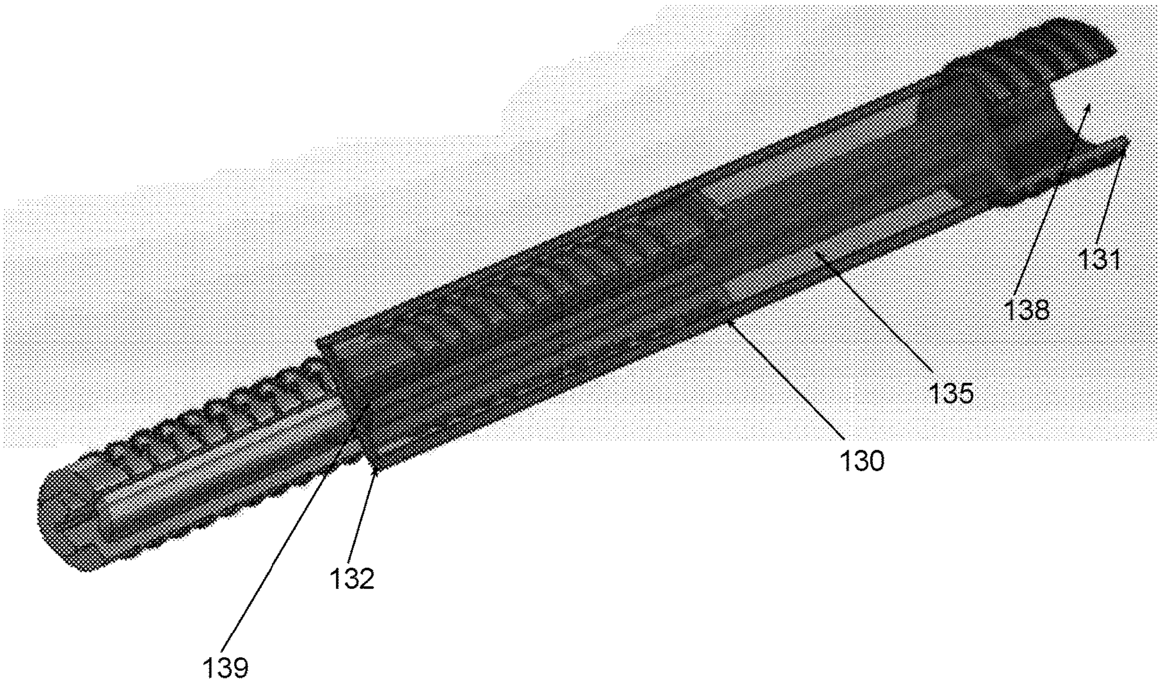
Figure 6D:
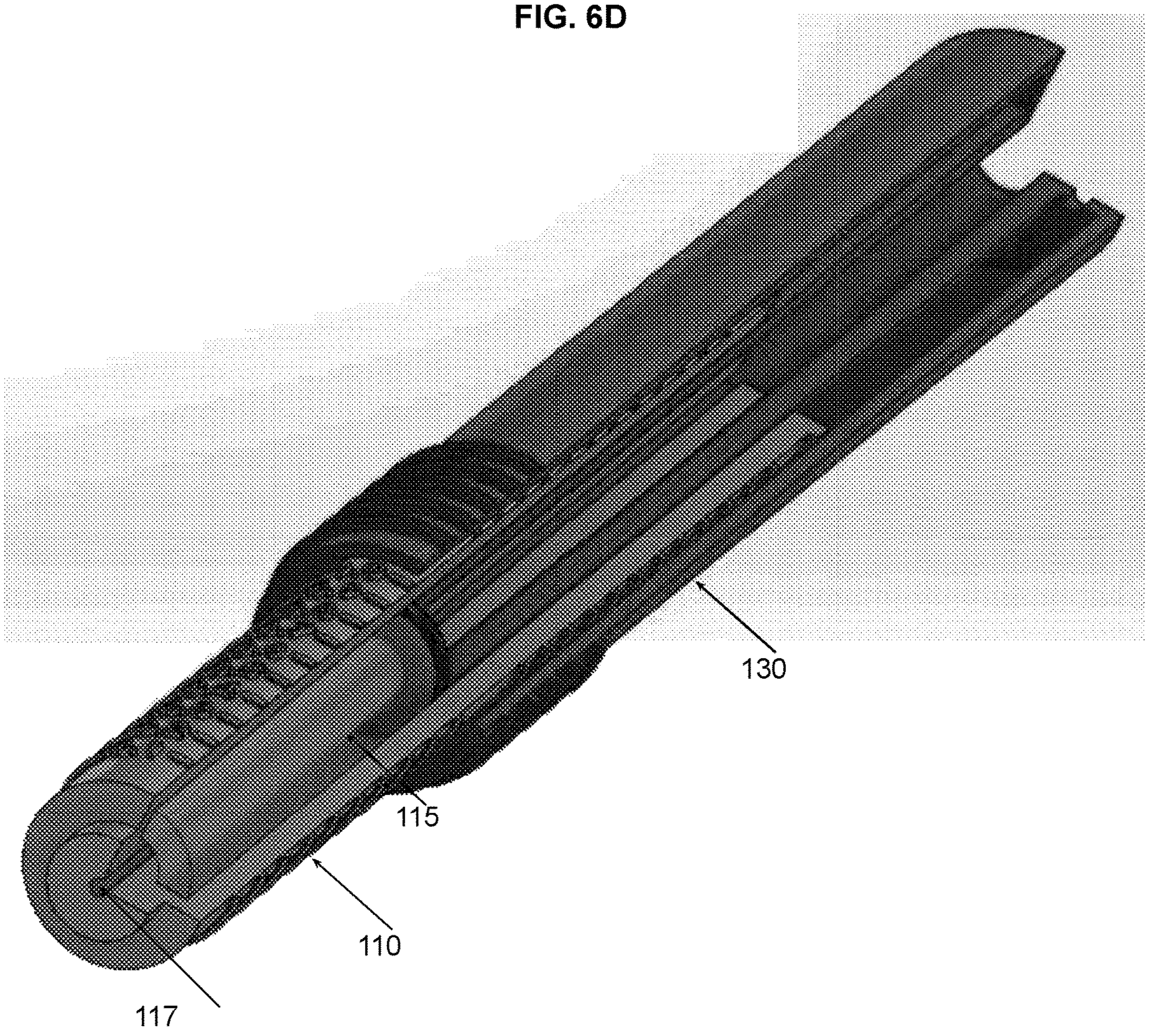
Figure 6E:
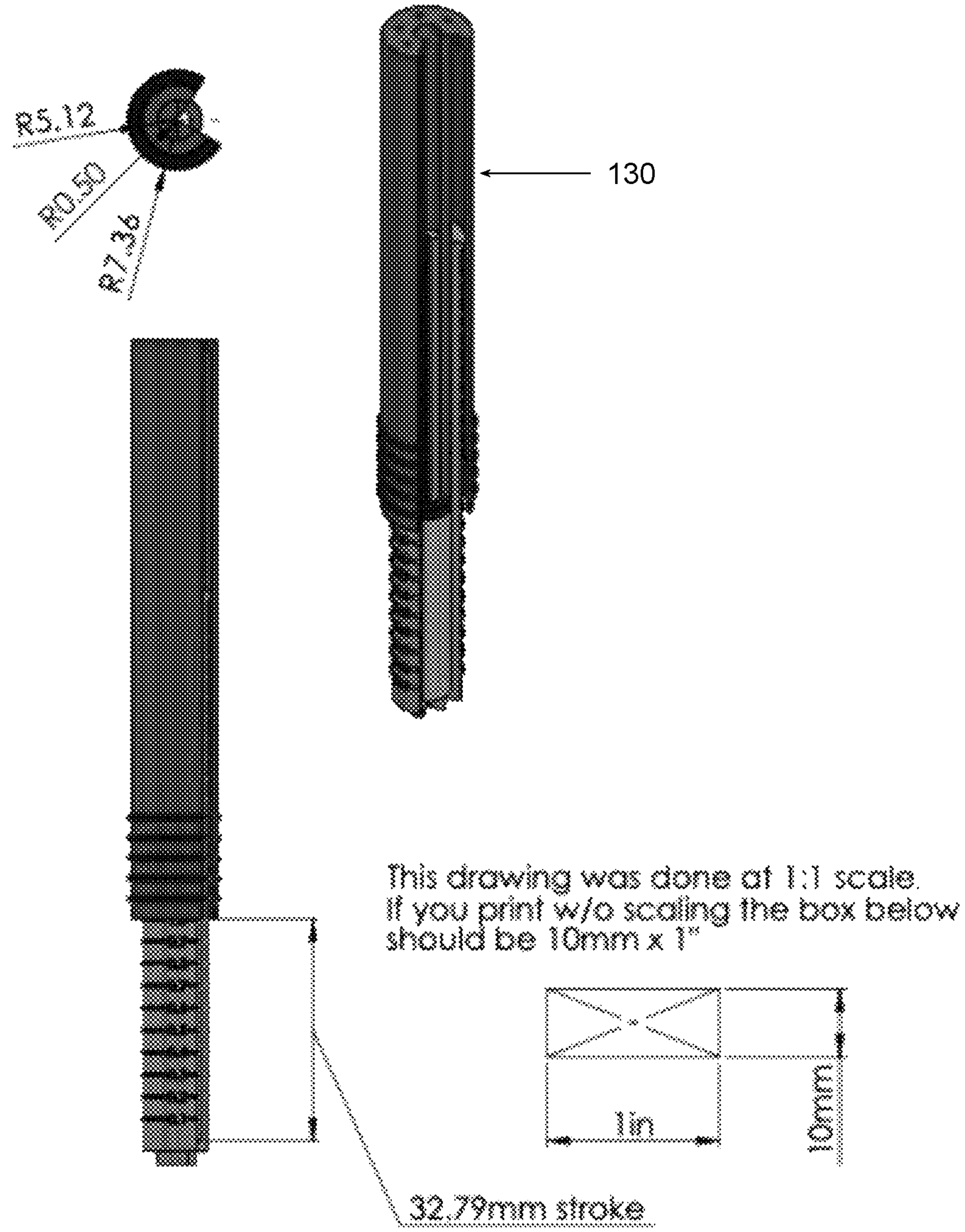
Figure 6F:
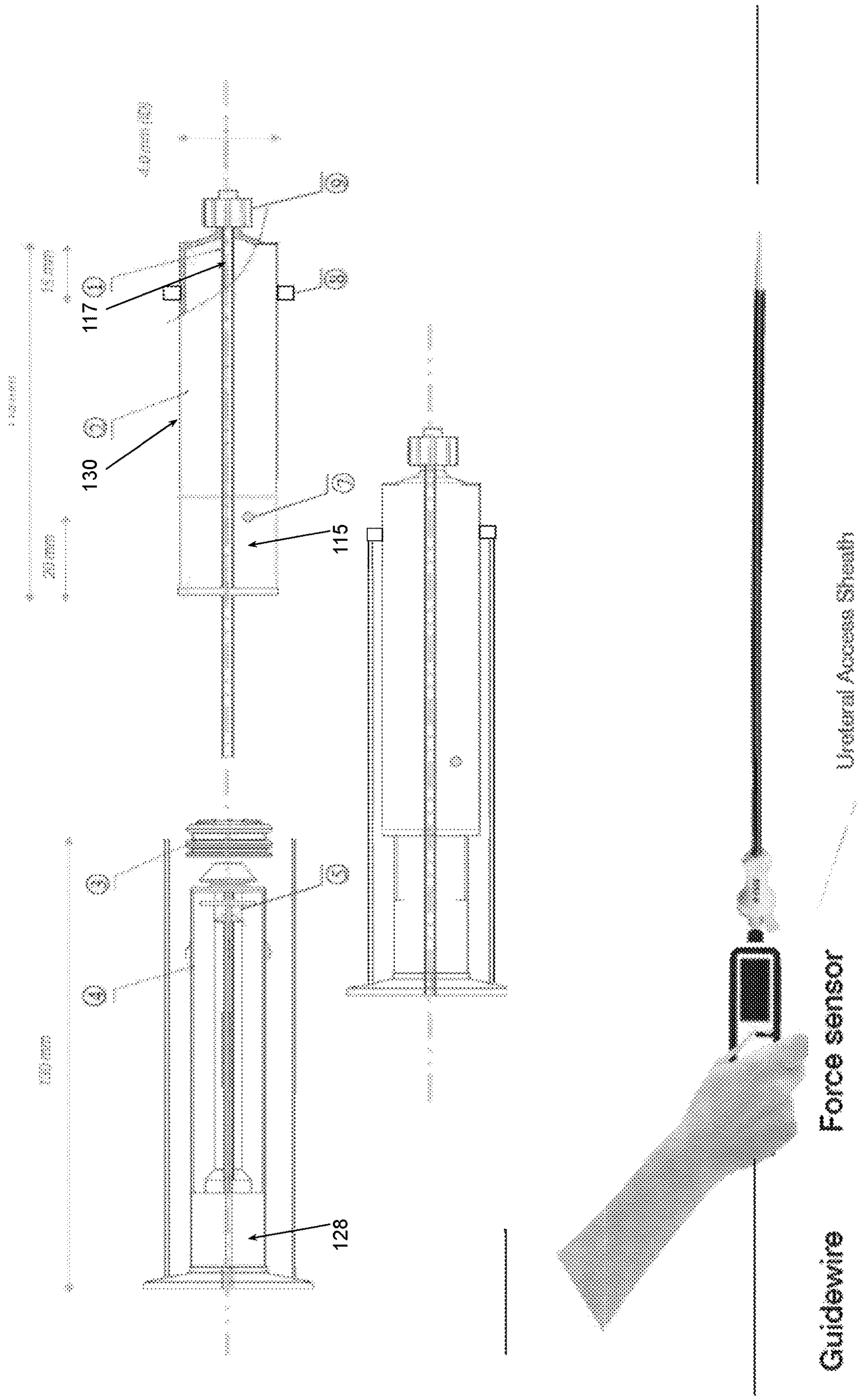

Luer-Lok™ Syringe (Becton Dickinson, Franklin Lakes, NJ): A force of 4 N, 6 N, and 8 N compressed the occluded syringe to a mean volume of 0.295±0.010 mL, 0.198=0.006 mL, and 0.145±0.006 mL, respectively. The measurements were consistent across different replicates of the same syringe at force thresholds of 4 N ($p=0.11$), 6 N ($p=0.36$), and 8 N ($p=0.26$), as assessed by an analysis of variance and Tukey post-hoc analysis (FIG. 5).

Tuberculin Syringe (Becton Dickinson, Franklin Lakes, NJ): A force of 4 N, 6 N, and 8 N compressed the occluded syringe to a mean volume of 0.332±0.019 mL, 0.219=0.013 mL, and 0.152±0.014 mL, respectively. The measurements were less consistent across different replicates of the same syringe at force thresholds of 4 N, 6 N, and 8 N. ANOVA and Tukey post-hoc analysis between five replicate syringes of the same brand showed statistically significant differences at all force thresholds (4 N, $p=0.0005$; 6 N, $p=0.0001$; 8 N, $p=0.001$) (FIG. 5).

Luer Slip Syringe (Berpu Medical Technology, Zhejiang, China): A force of 4 N, 6 N, and 8 N compressed the occluded syringe to a mean volume of 0.307±0.009 mL, 0.214±0.010 mL, and 0.164±0.006 mL, respectively. The measurements were less consistent across different replicates of the same syringe at force thresholds of 4 N, 6 N, and 8 N. ANOVA and Tukey post-hoc analysis between five replicate syringes of the same brand showed statistically significant differences at all force thresholds (4 N, p=0.0001; 6 N, p=0.0001; 8 N, p=0.0010) (FIG. 3).

Overall syringes: The Luer-Lok™ Syringe displayed the most consistent results, with a statistically significantly lower standard deviation, at all three force threshold levels, as assessed by multiple independent samples two-tailed F-tests (FIG. 63). For the Luer-Lok™ syringe specifically, compressing the syringe to a volume of 0.30 mL, 0.20 mL, and 0.15 mL corresponds to a force of 4 N, 6 N, and 8 N, respectively. For the other two syringes, regardless of brand, there was more variability among results. Compressing the two syringes to a volume of 0.4 mL, 0.25 mL, and 0.20 mL ensures that ureteral access sheath insertion force never exceeds 4 N, 6 N, and 8 N, respectively.

The above-described laboratory studies introduce an innovative, accessible, and cost-effective force sensor named "air-force one," designed to assist urologists in monitoring the surgical force applied during the deployment of UAS during retrograde intrarenal surgery (RIRS). This novel sensor is predicated on the principles of Boyle's Law and offers a pragmatic solution to the limitations presented by the more complex UCI-FS.

The benchtop testing results indicate that "air-force one" can reliably estimate the surgical force applied on an occluded 1 mL syringe based on volume change, providing a simple yet effective method for urologists to avoid exerting excessive force during UAS insertion. The force thresholds identified for the Luer Lock syringe—0.30 mL for 4 N, 0.20 mL for 6 N, and 0.15 mL for 8 N—are of paramount importance, with forces exceeding 8 N associated with high-grade injuries in prior clinical studies.

The comparative analysis of three different brands of 1 mL syringes revealed consistent measurements within each brand, but most of all with the Luer-Lok™ Syringe (Becton Dickinson, Franklin Lakes, NJ), and established a reproducible relationship between applied force and volume displacement. The Luer-Lok™ syringe displayed no significant variability across multiple tests at all force thresholds underscoring its potential as a reliable instrument. Although the Tuberculin Syringe (Becton Dickinson, Franklin Lakes, NJ) and Luer Slip Syringe (Berpu Medical Technology, Zhejiang, China) demonstrated a wider range in testing, compressing the two syringes to a volume of 0.40 mL, 0.25 mL, and 0.20 mL ensures that UAS insertion force never exceeds 4 N, 6 N, and 8 N, respectively. Therefore, as a rule of thumb, 0.20 mL should be a cut-off for all three syringes, with the Luer-Lok™ Syringe precisely reaching 6 N and the Tuberculin and Luer Slip Syringe reaching up to (but less than) 8 N. Both situations would avoid a surgical force of greater than 8 N thereby avoiding a high-grade ureteral injury.

The small difference in mean volume to reach the force thresholds between syringe brands (i.e., for 6 N Luer-Lok™ Syringe 0.20 mL, Tuberculin Syringe 0.22 mL, Luer Slip Syringe 0.21 mL) is likely due to the difference in the inner plunger surface area of the syringe brands thus affecting pressure-volume relationships (Luer-Lok™ Syringe ID 4.8 mm, Tuberculin Syringe 4.5 mm and Luer Slip Syringe ID 4.6 mm).

A 1 mL Luer-Lok™ Syringe was occluded with a BD Luer Tip Cap and Dermabond or Mastisol liquid adhesive. The 1 mL Luer-Lok™ Syringe is then clamped to the inner portion of a 20 or 30 mL Luer-Lok™ Syringe in which the specific plunger has been removed (Becton Dickinson, Franklin Lakes, NJ). The end of the larger syringe can then be passed over the guidewire, which passes through the obturator end of a UAS. The surgeon supports the UAS with one hand and then places constant pressure on the 1 ml syringe with the other hand until 0.2 mL is reached, indicating 6 N of force. All components are available in the operating room and can be rapidly assembled (FIG. 3).

It is noteworthy that the "air-force one" sensor embodies a user-friendly design, requiring minimal setup and no electronic components, differing markedly from the UCI-FS. This democratizes the ability to measure surgical force, potentially lowering the incidence of ureteral injuries globally by providing a universally accessible tool.

While designed to monitor surgical force during instrument insertion up the ureter, other possible applications may include situations in which a guidewire is not preplaced, such as Veress needle entry of the abdomen, laparoscopic trocar placement, percutaneous renal access or deployment of surgical retractors (in order to preclude tearing of the retracted tissue) as well as the passage of a variety of endoscopes be they rigid or flexible safely into any bodily orifice. Furthermore, this concept is beneficial in resident education. By using an occluded 1 ml syringe as a model, a urologist in training can be taught an appropriate amount of force to apply on a UAS during insertion.

Despite the promise shown by "air-force one," there are limitations to consider. The application of Boyle's law assumes an ideal gas and can be influenced by the atmospheric pressure of the operating room. To this end, Boyle's law was applied to compare Belgrade (the city with the highest barometric pressure in the world, 102.84 kPa) to Anchorage (the city with the lowest barometric pressure in the world, 98.51 kPa). The calculations demonstrate the extremes of atmospheric pressure in these two cities would result in only a small theoretical difference of </=0.02 mL in syringe thresholds in the case of assessing 4 N, 6 N, or 8 N. To note, all testing in this study occurred in Orange, CA, a city close to sea level with a barometric pressure of 101.66 kPa.

In conclusion, pushing an occluded 1 mL Luer-Lok™ Syringe (Becton Dickinson, Franklin Lakes, NJ) from 1 mL to 0.30 mL, 0.20 mL, and 0.15 mL takes precisely 4 N, 6 N and 8 N of force. The Tuberculin Syringe (Becton Dickinson, Franklin Lakes, NJ) and Luer Slip Syringe (Berpu Medical Technology, Zhejiang, China) demonstrated a wider range in testing but compressing from 1 mL to 0.40 mL, 0.25 mL, and 0.20 mL ensures that force never exceeds 4 N, 6 N, and 8 N, respectively.

Example 2

The following is a non-limiting example of the present invention. It is to be understood that said example is not intended to limit the present invention in any way. Equivalents or substitutes are within the scope of the present invention.

Testing was carried out to determine the force required to compress occluded syringes of multiple volumes.

Methods: Becton Dickinson 3 mL, 5 mL, 10 mL, 20 mL, and 50 mL syringes were acquired. The plunger of each syringe was drawn back to its maximum volume then occluded with a Becton Dickinson Luer Tip Cap. The occluded syringe was then compressed at a constant rate against a flat surface with a digital force gauge (Mxmoonfree Co., Guangdong, China) capable of measuring up to 50 Newtons (N) to a hundredth of a N.

The peak force required to reach each major gradation of the syringe was recorded, progressing to each subsequent lower major gradation until 50 N of force was reached. Testing for each syringe was run in quintuplicates. Results were then averaged and plotted in FIG. 60.

TABLE 1

| Results: BD 3 mL Syringe | |
|---|---|
| Volume of Air Compressed, mL | Mean Force Required to Compress Plunger, N (SD) |
| 0.5 | 5.06 (0.32) |
| 1.0 | 9.01 (0.48) |
| 1.5 | 16.78 (0.24) |
| 2.0 | 38.25 (0.36) |
| 2.5 | 50.61 (0.27) |
| 2.7 | 52.36 (1.37) |

TABLE 2

| Results: BD 5 mL Syringe | |
|---|---|
| Volume of Air Compressed, mL | Mean Force Required to Compress Plunger, N (SD) |
| 1.0 | 5.06 (0.32) |
| 2.0 | 9.01 (0.48) |
| 3.0 | 16.78 (0.24) |
| 4.0 | 38.25 (0.36) |
| 4.2 | 50.61 (0.27) |

TABLE 3

| Results: BD 10 mL Syringe | |
|---|---|
| Volume of Air Compressed, mL | Mean Force Required to Compress Plunger, N (SD) |
| 1.0 | 4.33 (0.22) |
| 2.0 | 6.51 (0.12) |
| 3.0 | 9.28 (0.40) |
| 4.0 | 13.40 (0.26) |
| 5.0 | 18.53 (0.22) |
| 6.0 | 26.83 (0.46) |
| 7.0 | 39.48 (0.44) |
| 7.2 | 50.39 (0.20) |

TABLE 4

| Results: BD 20 mL Syringe | |
|---|---|
| Volume of Air Compressed, mL | Mean Force Required to Compress Plunger, N (SD) |
| 5.0 | 18.09 (0.54) |
| 10.0 | 36.46 (0.79) |
| 12.0 | 50.70 (0.49) |

TABLE 5

| Results: BD 50 mL Syringe | |
|---|---|
| Volume of Air Compressed, mL | Mean Force Required to Compress Plunger, N (SD) |
| 10.0 | 19.34 (0.20) |
| 20.0 | 41.21 (0.90) |
| 23.0 | 50.55 (0.32) |

Discussion: The relationship between the volume of air compressed and force is directly related (i.e., force increases as the volume of air compressed increases) which supports the direct application of Boyle's Law. Although the force gauge only allowed for force measurements up to 50 N, larger volume syringes demonstrate the capability of measuring larger amounts of force. Accordingly, the choice of syringe volume for force measurement in the clinical setting is tailored to the desired force threshold (i.e., a 1 ml syringe for 8 N and a 5 mL syringe for 30 N). Additionally, as the total syringe volume is exhausted, the force required to compress the plunger increases exponentially (i.e., the slope of the line of best fit increases). This may affect accuracy given that a small change in stroke volume at this point requires an even larger amount of force. This suggests each syringe volume may have a "sweet spot" whereby the force threshold desired should be located just before the exponential increase in force but still allow for an adequate amount of stroke to reach the force threshold. Finally, within the same volume of syringe, there were only small variations of force seen between replicates within the same volume of compressed air. This indicates precision.

Example 3

The following is a non-limiting example of the present invention. It is to be understood that said example is not intended to limit the present invention in any way. Equivalents or substitutes are within the scope of the present invention.

Methods: Referring to FIG. 61-62, five 1.0 mL syringes from three brands (BD, Luer-Lok™, BD Tuberculin, and Berpu Leur Slip) were tested. Syringes were occluded at 1.0 mL, and plungers were compressed at a constant rate while measuring force in hundreds of a N. Forces of 4 N, 6 N, and 8 N were correlated with the plunger's descent at specific millimeter graduations. Testing for each individual syringe was performed in quintuplicates, yielding 225 measurements. The BD Luer-Lok™ syringe provided the most reproducible measurements. The BD Luer-Lok syringe was combined with a barrel of a 20 mL syringe to create Air Force #1. Air Force #1 was used to insert a UAS at <8 N among 21 patients with renal stones.

Results: Force thresholds of 4 N, 6 N, and 8 N were recorded with the 1.0 mL BD Luer-Lok™ syringe at 0.30 mL, 0.20 mL, and 0.15 mL, respectively. In 20 patients, the Air Force #1 provided safe passage of the UAS to the renal pelvis/proximal ureter. In 29% of patients, a 16 Fr UAS was utilized. No transmural tears of the ureter were observed in post-procedure ureteroscopy (≥Post Ureteroscopic Lesion Score; PULS).

TABLE 6

Clinical usage data for the Air Force Sensor with zero high-grade ureteral injuries in 21 patients.
Baseline demographics and intraoperative details for RIRS/PCNL patients undergoing UAS Insertion with Air Force #1 sensor.

| Demographics | | |
|---|---|---|
| Age, years (SD) | | 66.33 (9.48) |
| BMI, kg/m$^2$ (SD) | | 29.63 (7.52) |
| Gender | Male | 15 (71.4%) |
| | Female | 6 (28.6%) |
| Intraoperative Details | | |
| Procedure | URS | 12 (57.1%) |
| | PCNL | 9 (42.8%) |
| Laterality | Left | 13 (61.9%) |
| | Right | 8 (38.1%) |
| Pre-stented | Yes | 7 (33.3%) |
| | No | 14 (66.6%) |

TABLE 6-continued

Clinical usage data for the Air Force Sensor with zero high-grade ureteral injuries in 21 patients.
Baseline demographics and intraoperative details for RIRS/PCNL patients undergoing UAS Insertion with Air Force #1 sensor.

| | | |
|---|---|---|
| UAS size (Fr) | No UAS | 1 (4.8%) |
| | 12 | 8 (38.1%) |
| | 14 | 6 (28.6%) |
| | 16 | 6 (28.6%) |
| PULS Grading | 0 | 2 (10.0%) |
| (3 = transmural ureteral tear; | 1 | 17 (85.0%) |
| one ureter not assessed) | 2 | 1 (5.0%) |
| | 3 | 0 (0.0%) |
| UAS Insertion Force (N) | ≤4 | 7 (41.2%) |
| (n = 4 not recorded) | <4-≤6 | 8 (47.1%) |
| | >6-<8 | 2 (11.8%) |

Conclusion: Using an occluded BD Luer-Lok™ 1.0 mL syringe, forces of 4 N, 6 N, and 8 N could be reliably measured. Among 21 patients undergoing UAS passage, the Air Force #1 sensor precluded any high-grade ureteral injuries.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

Reference numbers recited herein, in the drawings, and in the claims are solely for ease of examination of this patent application and are exemplary. The reference numbers are not intended in any way to limit the scope of the claims to the particular features having the corresponding reference numbers in the drawings.

What is claimed is:

1. A force sensing device (100) for monitoring an insertion force of a medical device, the device comprising:

a) a tube (110) comprising a first end (111), a second end (112), a first lumen (115), and a second lumen (117); each lumen disposed within the tube (110) and extending at least partially between the first end (111) and the second end (112); wherein the first end (111) comprises an opening (118) and the second end (112) comprises an interface for attaching the medical device; wherein the first lumen (115) is airtight, b) a plunger (120) comprising a first plunger end (121) disposed through the opening (118) of the tube (110) and within the first lumen (115);

c) an outer casing (130) comprising a lumen (135), wherein at least a portion of the tube (110) and at least a portion of the plunger (120) are disposed within the lumen (135); and d) one or more visual indicators disposed on at least a portion of the second end (112) of the tube (110), the visual indicators being configured to indicate the applied force relating to the displacement of the plunger (120), wherein an insertion force applied to the medical device and transmitted through the force sensing device (100) is sensed by detecting the displacement of the plunger (120) and the resulting compression of a fluid within the first lumen (115) of the tube (110) during insertion of a medical device attached to the force sensing device (100);

wherein the fluid is air or a liquid.

2. The device (100) of claim 1, wherein the second lumen (117) is disposed within the first lumen (115); wherein the second lumen (117) is centrally disposed within the first lumen (115) of the tube (110).

3. The device (100) of claim 2, wherein the plunger (120) is slidably coupled to the second lumen (117), and wherein a plunger lumen (125) and the second lumen (117) of the tube (110) are fluidly coupled allowing a guidewire to pass through both lumens.

4. The device (100) of claim 1, wherein the second lumen (117) is a guidewire lumen through which a guidewire may be passed therethrough; wherein the guidewire directs the force sensing device (100) and/or medical device being inserted.

5. The device (100) of claim 1, wherein the medical device is a ureteral access sheath (UAS), a rigid or flexible endoscope, a Foley catheter, or an intravenous line.

6. The device (100) of claim 1, wherein the medical device is a laparoscopic surgical device, a laparoscopic trocar, a robotic surgical device, a minimally invasive surgical device, a Veress needle, a percutaneous renal access device, or a surgical retractor.

7. The device (100) of claim 1, wherein the interface comprises a Luer-Lock style interface.

8. The device (100) of claim 1, wherein the interface comprises a pressure fitting interface, a Luer Slip style interface, or a twist-to-connect coupling interface.

9. The device (100) of claim 1, wherein the interface is positioned distal to ureteral access sheath (UAS) point of insertion.

10. The device (100) of claim 1, wherein the device (100) is a pneumatic device and the fluid is air.

11. The device (100) of claim 1, wherein the device (100) is a hydraulic device and the fluid is liquid.

12. A method of monitoring an insertion force of a medical device, the method comprising:

a) attaching the medical device to a force sensing device (100) comprising:

i. a tube (110) comprising a first end (111), a second end (112), a first lumen (115), and a second lumen (117); each lumen disposed within the tube (110) and extending at least partially between the first end (111) and the second end (112); wherein the first end (111) comprises an opening (118) and the second end (112) comprises an interface for attaching the medical device; wherein the first lumen (115) is essentially airtight, ii. a plunger (120) comprising a first plunger end (121), disposed through the opening (118) of the tube (110) and within the first lumen (115);

iii. an outer casing (130) comprising a lumen (135), wherein at least a portion of the tube (110) and at least a portion of the plunger (120) are disposed within the lumen (135); and iv. one or more visual indicators disposed on at least a portion of the second end (112) of the tube (110), the visual indicators being configured to indicate the applied force relating to the displacement of the plunger (120); wherein a distal end of the medical device is attached to the interface of the force sensing device (100), b) inserting the medical device attached to the force sensing device (100) into a patient; and c) monitoring an insertion force of the medical device attached to the force sensing device (100) by detecting the displacement of the plunger (120) and the resulting compression of a fluid within the first lumen (115) of the tube (110), wherein as the plunger (120) of the force sensing device (100) is pushed towards the second end (112) of the tube (110) during the insertion of the medical device attached to the force sensing device (100) into the patient, the plunger (120) compresses the fluid within the first lumen (115) of the tube (110), wherein displacement of the plunger (120) varies continuously with changes in the insertion force;

wherein the fluid is air or a liquid.

13. The method of claim 12, wherein the medical device is a laparoscopic surgical device, a laparoscopic trocar, a robotic surgical device, a minimally invasive surgical device, a Veress needle, a percutaneous renal access device, or a surgical retractor.

14. The method of claim 12, wherein the medical device is a ureteral access sheath (UAS), a rigid or flexible endoscope, a Foley catheter, or an intravenous line.

15. The method of claim 12, wherein the device (100) is a pneumatic device and the fluid is air.

16. The method of claim 12, wherein the device (100) is a hydraulic device and the fluid is liquid.

17. A force sensing device (100) for monitoring an insertion force of a medical device, the device comprising:

a) a tube (110) comprising a first end (111), a second end (112), a first lumen (115), and a second lumen (117); each lumen disposed within the tube (110) and extending at least partially between the first end (111) and the second end (112); wherein the first end (111) comprises an opening (118) and the second end (112) comprises an interface for attaching the medical device; wherein the first lumen (115) is a sealed, closed fluid chamber configured to resist fluid exchange with an external environment during insertion, b) a plunger (120) comprising a first plunger end (121) disposed through the opening (118) of the tube (110) and within the first lumen (115), the plunger (120) being configured to translate axially along a longitudinal axis of the tube (110);

c) an outer casing (130) comprising a lumen (135), wherein at least a portion of the tube (110) and at least a portion of the plunger (120) are disposed within the lumen (135); and d) one or more visual indicators disposed on at least a portion of the second end (112) of the tube (110), the visual indicators being configured to indicate the applied force relating to the displacement of the plunger (120), the visual indicators being configured to provide real-time visual feedback during advancement of the medical device;

wherein an insertion force applied to the medical device and transmitted through the force sensing device (100) is sensed by detecting the displacement of the plunger (120) and the resulting compression of a fluid within the first lumen (115) of the tube (110) during insertion of a medical device attached to the force sensing device (100), wherein displacement of the plunger (120) varies continuously with changes in the insertion force, wherein the fluid is air or a liquid.

* * * * *